US 7,416,738 B2

(12) United States Patent
Sowden et al.

(10) Patent No.: US 7,416,738 B2
(45) Date of Patent: Aug. 26, 2008

(54) MODIFIED RELEASE DOSAGE FORM

(75) Inventors: Harry S. Sowden, Glenside, PA (US);
Gerard P. McNally, Berwyn, PA (US);
David Wynn, Abington, PA (US); Oliver Anderson, Willow Grove, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 616 days.

(21) Appl. No.: 10/393,871

(22) Filed: Mar. 21, 2003

(65) Prior Publication Data

US 2003/0235616 A1 Dec. 25, 2003

Related U.S. Application Data

(63) Continuation-in-part of application No. PCT/US02/31129, filed on Sep. 28, 2002, and a continuation-in-part of application No. PCT/US02/31117, filed on Sep. 28, 2002, and a continuation-in-part of application No. PCT/US02/31062, filed on Sep. 28, 2002, and a continuation-in-part of application No. PCT/US02/31024, filed on Sep. 28, 2002, and a continuation-in-part of application No. PCT/US02/31163, filed on Sep. 28, 2002, which is a continuation-in-part of application No. 09/966,939, filed on Sep. 28, 2001, now Pat. No. 6,837,696, and a continuation-in-part of application No. 09/966,509, filed on Sep. 28, 2001, now Pat. No. 6,767,200, and a continuation-in-part of application No. 09/966,497, filed on Sep. 28, 2001, and a continuation-in-part of application No. 09/967,414, filed on Sep. 28, 2001, now Pat. No. 6,742,646, and a continuation-in-part of application No. 09/966,450, filed on Sep. 28, 2001, now Pat. No. 6,982,094.

(51) Int. Cl.
*A61K 9/22* (2006.01)
*A61K 9/24* (2006.01)
*A61K 9/26* (2006.01)

(52) U.S. Cl. .................. 424/471; 424/464; 424/465; 424/467; 424/474

(58) Field of Classification Search .......... 424/471, 424/464, 465, 467, 474
See application file for complete search history.

(56) References Cited

U.S. PATENT DOCUMENTS

| | | | |
|---|---|---|---|
| 3,185,626 A | 5/1965 | Baker | |
| 3,760,804 A | 9/1973 | Higuchi et al. | |
| 3,845,770 A * | 11/1974 | Theeuwes et al. | 424/427 |
| 4,449,983 A | 5/1984 | Cortese et al. | |
| 4,543,370 A | 9/1985 | Porter et al. | |
| 4,576,604 A | 3/1986 | Guittard et al. | |
| 4,643,894 A | 2/1987 | Porter et al. | |
| 4,683,256 A | 7/1987 | Porter et al. | |
| 4,725,441 A | 2/1988 | Porter et al. | |
| 4,801,461 A | 1/1989 | Hamel et al. | |
| 4,802,924 A | 2/1989 | Woznicki et al. | |
| 4,816,262 A | 3/1989 | McMullen | |
| 4,828,841 A | 5/1989 | Porter et al. | |
| 4,857,330 A | 8/1989 | Stephens et al. | |
| 4,865,849 A | 9/1989 | Conte et al. | |
| 4,906,478 A | 3/1990 | Valentine et al. | |
| 5,275,822 A | 1/1994 | Valentine et al. | |
| 5,427,614 A | 6/1995 | Wittwer et al. | |
| 5,464,633 A | 11/1995 | Conte et al. | |
| 5,558,879 A * | 9/1996 | Chen et al. | 424/480 |
| 5,630,871 A | 5/1997 | Jordan | |
| 5,658,589 A | 8/1997 | Parekh et al. | |
| 5,738,874 A | 4/1998 | Conte et al. | |
| 6,103,260 A | 8/2000 | Luber et al. | |
| 6,110,499 A | 8/2000 | Shivanand et al. | |
| 6,264,985 B1 | 7/2001 | Cremer | |
| 6,274,162 B1 | 8/2001 | Steffenino et al. | |
| 6,365,185 B1 | 4/2002 | Ritschel et al. | |
| 2002/0028240 A1 | 3/2002 | Sawada et al. | |
| 2002/0051807 A1 | 5/2002 | Faour et al. | |

FOREIGN PATENT DOCUMENTS

| | | |
|---|---|---|
| EP | 0 325 492 A1 | 7/1989 |
| GB | 759081 | 10/1956 |
| WO | WO 99/62496 | 12/1999 |
| WO | WO 00/18447 | 4/2000 |
| WO | WO 02/11702 A2 | 2/2002 |
| WO | WO 02/066015 A1 | 8/2002 |
| WO | WO 03/020246 A1 | 3/2003 |

OTHER PUBLICATIONS

Liberman, et al., *Pharmaceutical Dosage Forms—Tablets*, 1990, pp. 213-217; 327-329; vol. 2, 2nd ed., Markel Dekker Inc., New York.
Elizabeth Carbide Die Co., Inc., *The Elizabeth Companies Tablet Design Training Manual*, p. 7, McKeesport, PA.
Lachman, et al., *The Theory and Practice of Industrial Pharmacy*, 1986, Chapter 11, 3rd ed.
Eith, L., et al., "Injection-Moulded Drug-Delivery Systems", *Manufacturing Chemist* (Jan. 1987), pp. 21-25.
International Search Report dated Jan. 8, 2004 for corresponding PCT/US03/08891.
McNeil-PPC, Inc., 02/31129.

(Continued)

*Primary Examiner*—Johann Richter
(74) *Attorney, Agent, or Firm*—David Crichton

(57) ABSTRACT

A modified release dosage form comprising at least one active ingredient and at least two cores surrounded by a shell is provided. The shell comprises at least one opening and provides for modified release of active ingredient upon contacting of the dosage form with a liquid medium. At least one of the cores is distal from the opening. In a preferred embodiment, the dosage form has a pulsatile release profile.

45 Claims, 4 Drawing Sheets

OTHER PUBLICATIONS

McNeil-PPC, Inc., 02/31117.
McNeil-PPC, Inc., 02/31062.
McNeil-PPC, Inc., 02/31024.
McNeil-PPC, Inc., 02/31163.
McNeil-PPC, Inc., 09/966,939.
McNeil-PPC, Inc., 09/966,509.
McNeil-PPC, Inc., 09/966,497.
McNeil-PPC, Inc., 09/967,414.
McNeil-PPC, Inc., 09/966,450.
Chueshov V.I. et al., Industrial Technology of Medicaments. A textbook in two volumes vol. 2, Drug Manufacturing Technology, edited by Cheushov V.I., Ch: Osnova publishers, 1999.
PCT Search Report dated Aug. 19, 2003, for PCT Appl. No. PCT/US 03/08894.

* cited by examiner

MODIFIED RELEASE DOSAGE FORM

CROSS-REFERENCE TO RELATED APPLICATIONS

This application is a Continuation-in-part of PCT/US02/31024, filed Sep. 28, 2002, pending, which is a Continuation-in-part of PCT/US02/31062, filed Sep. 28, 2002, pending, which is a Continuation-in-part of PCT/US02/31117, filed Sep. 28, 2002, pending, which is a Contination-in-part of PCT/US02/31129, filed Sep. 28, 2002, pending, which in a Continuation-in-part of PCT/US02/31163, filed Sep. 28, 2002, pending, which is a Continuation-in-part of U.S. Ser. No. 09/966,939, filed Sep. 28, 2001, patented as U.S. Pat. No. 6,837,696, which is a Continuation-in-part of 09/966,450, filed Sep. 28, 2001, patented as U.S. Pat. No. 6,982,094, which is a Continuation-in-part of 09/966,509, filed Sep. 28, 2001, patented as U.S. Pat. No. 6,767,200, which is a Continuation-in-part of 09/966,497, filed Sep. 28, 2001, patented as U.S. Pat. No. 7,122,143, and which is a Continuation-in-part of 09/967,414, filed Sep. 28, 2001, patented as U.S. Pat. No. 6,742,646.

FIELD OF THE INVENTION

This invention relates to dosage forms providing modified release of active ingredient contained therein. The dosage forms comprise two or more cores surrounded by a shell having one or more openings. The opening or openings are distal to at least one of the cores. Preferably, the opening or openings are proximal to at least one core and distal to at least another core.

BACKGROUND OF THE INVENTION

Modified release pharmaceutical dosage forms have long been used to optimize drug delivery and enhance patient compliance, especially by reducing the number of doses of medicine the patient must take in a day. In some instances, it is also desirable for a dosage form to deliver more than one drug at different rates or times. Modified release dosage forms should ideally be adaptable so that release rates and profiles can be matched to physiological and chronotherapeutic requirements. Because the onset and duration of the therapeutic efficacy of drugs vary widely, as do their absorption, distribution, metabolism, and elimination, it is often desirable to modify the release of different drugs in different ways, or to have a first dose of drug (active ingredient) immediately released from the dosage form, while a second dose of the same or a different drug is released in a modified, e.g. delayed, pulsatile, repeat action, controlled, sustained, prolonged, extended, or retarded manner.

Well known mechanisms by which a dosage form (or drug delivery system) can deliver drug at a controlled rate (e.g. sustained, prolonged, extended or retarded release) include diffusion, erosion, and osmosis. It is often practical to design dosage forms that use a combination of the above mechanisms to achieve a particularly desirable release profile for a particular active ingredient. It will be readily recognized by those skilled in the art that a dosage form construct which offers multiple compartments, such as for example multiple core portions and/or multiple shell portions, is particularly advantageous for its flexibility in providing a number of different mechanisms for controlling the release of one or more active ingredients.

An important objective of modified release dosage forms is to provide a desired blood concentration versus time (pharmacokinetic, or PK) profile for the drug. Fundamentally, the PK profile for a drug is governed by the rate of absorption of the drug into the blood, and the rate of elimination of the drug from the blood. To be absorbed into the blood (circulatory system), the drug must first be dissolved in the g.i. fluids. For those relatively rapidly absorbed drugs whose dissolution in g.i. fluids is the rate limiting step in drug absorption, controlling the rate of dissolution (i.e. drug release from the dosage form) allows the formulator to control the rate of drug absorption into the circulatory system of a patient. The type of PK profile, and correspondingly, the type of dissolution or release profile desired, depends on, among other factors, the particular active ingredient and physiological condition being treated.

One particularly desirable PK profile is achieved by a dosage form that delivers a delayed release dissolution profile, in which the release of one or more doses of drug from the dosage form is delayed for a pre-determined time after contacting of the dosage form by a liquid medium, such as for example, after ingestion by the patient. The delay period ("lag time") can be followed either by prompt release of the active ingredient ("delayed burst"), or by sustained (prolonged, extended, or retarded) release of the active ingredient ("delayed then sustained"). U.S. Pat. No. 5,464,633, for example, discloses delayed-release dosage forms in which an external coating layer was applied by a compression coating process. The coating level ranged from 105 percent to 140 percent of the weight of the core in order to yield product with the desired time delayed profile.

One particularly desirable type of delayed release PK profile is obtained from a "pulsatile" release profile, in which for example, a first dose of a first drug is delivered, followed by a delay period ("lag time") during which there is substantially no release of the first drug from the dosage form, followed by either prompt or sustained release of a subsequent dose of the same drug. In one particularly desirable type of pulsatile drug delivery system, the first dose is released essentially immediately upon contacting of the dosage form with a liquid medium. In another particularly desirable type of pulsatile drug delivery system, the delay period corresponds approximately to the time during which a therapeutic concentration of the first dose is maintained in the blood. Pulsatile delivery systems are particularly useful for applications where a continuous release of drug is not ideal. Examples of this are drugs exhibiting first pass metabolism by the liver, drugs that induce biological tolerance, i.e. the therapeutic effect decreases with continuous presence of the drug at the site of action, and drugs whose efficacy is influenced by circadian rhythms of body functions or diseases. One typical pulsatile dosage form design contains the first dose of drug in an exterior coating, or shell, while subsequent doses of drug are contained in underlying layers of subcoatings, or a central core. PCT Publication No. WO99/62496, for example, discloses a dosage form comprising an immediate-release dose of drug contained within an overcoat applied onto the surface of the semipermeable membrane of an osmotic dosage form. U.S. Pat. Nos. 4,857, 330 and 4,801,461, disclose dosage forms comprising an exterior drug coat that surrounds a semipermeable wall, which in turn surrounds an internal compartment containing a second dose of drug, and comprises exit means for connecting the interior of the dosage form with the exterior environment of use. These dosage forms are designed to release drug immediately from the exterior coating, followed by a relatively short delay period, followed by a sustained release of drug from the internal compartment.

U.S. Pat. No. 4,576,604, for example, discloses an osmotic device (dosage form) comprising a drug compartment surrounded by a wall (coating) having an passageway therein.

The wall may comprise an immediate release dose of drug, and the inner drug compartment may comprise a sustained release dose of drug. U.S. Pat. No. 4,449,983 discloses another osmotic device comprising two separately housed drugs that are separately dispensed from the device. The device comprises two compartments, one for each drug, separated by a partition. Each compartment has an orifice for communicating with the exterior of the device. U.S. Pat. No. 5,738,874, discloses a 3-layer pharmaceutical compressed tablet capable of liberating one or more drugs at different release rates, in which an immediate release dose of active may be contained in a compressed coating layer, and in one embodiment, the outer compressed coating layer may function via an erosion mechanism to delay release of a second dose of active ingredient contained in the core. Systems such as these are limited by the amount of drug which may be incorporated into the exterior coating or shell, which is in turn limited by the achievable thickness of the exterior coating or shell.

Another design for a pulsatile delivery system is exemplified in U.S. Pat. No. 4,865,849, which describes a tablet able to release active substances at successive times, comprising a first layer containing a portion of the active substance, a water soluble or water gellable barrier layer which is interposed between the first layer and a third layer containing the remaining portion of active substance, and the barrier layer and third layer are housed in an insoluble, impermeable casing. The casing can be applied by various methods such as spraying, compression, or immersion, or the tablet parts can be inserted into a pre-formed casing. Multilayer compressed tablets in stacked layer configurations necessessarily require an impermeable partial coating (casing) in order to provide a pulsatile release profile. These systems suffer from the complexity and high cost of assembling multiple, separate compartments comprising multiple, different compositions.

Dosage forms have been previously designed with multiple cores housed in a single shell for the purpose of allowing flexibility in a dosing regimen. PCT Publication No. WO00/18447, for example, describes a multiplex drug delivery system suitable for oral administration containing at least two distinct drug dosage packages, which exhibit equivalent dissolution profiles for an active agent when compared to one another and when compared to that of the entire multiplex drug delivery unit, and substantially enveloped by a scored compressed coating that allows the separation of the multiplex drug delivery system into individual drug dosage packages. In this example, two immediate-release compartments are enveloped by a scored extended-release compartment. Active ingredient may be contained in only the extended release compartment, or additionally in the two immediate release compartments. The multiplex drug delivery systems of this example are prepared by press coating the extended-release compartment to substantially envelop the immediate release compartments.

Improved dosage forms for providing modified release of active ingredient are described herein. The dosage forms comprise at least one active ingredient and at least two cores surrounded by a shell, wherein the shell comprises one or more openings that are distal to one of the cores. Preferably, the opening or openings are proximal or connected to at least one core, but distal from at least another core. In this manner, at least one core communicates with the exterior of the dosage form through an opening, while at least another core therein does not. Upon contact with a liquid medium, active ingredient, which may be present in one or more of the cores, in the shell, or portions or combinations thereof, is released from the dosage form in a modified fashion.

SUMMARY OF THE INVENTION

The invention provides a dosage form comprising at least one active ingredient, a first core, and a second core, said first and second cores being surrounded by a shell, wherein the shell comprises one or more openings and provides for modified release of at least one active ingredient upon contact of the dosage form with a liquid medium, at least one of the first or second cores being distal to the opening or openings.

The invention also provides a dosage form comprising a first core containing a pharmaceutically effective dose of a first active ingredient, and a second core containing a pharmaceutically effective dose of a second active ingredient, said first and second cores each being surrounded by a shell, wherein the shell comprises a plurality of openings and provides for modified release of the second active ingredient upon contact of the dosage form with a liquid medium, wherein the second core is located distal to all the openings, and all the openings are proximal to only the first core.

DETAILED DESCRIPTION OF THE INVENTION

Figure 1A:
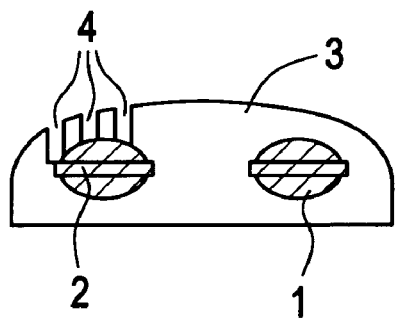
FIGS. 1A and 1B depict a dosage form according to the invention.

As used herein, the term "dosage form" applies to any solid object, semi-solid, or liquid composition designed to contain a specific pre-determined amount (dose) of a certain ingredient, for example an active ingredient as defined below. Suitable dosage forms may be pharmaceutical drug delivery systems, including those for oral administration, buccal administration, rectal administration, topical or mucosal delivery, or subcutaneous implants, or other implanted drug delivery systems; or compositions for delivering minerals, vitamins and other nutraceuticals, oral care agents, flavorants, and the like. Preferably the dosage forms of the present invention are considered to be solid, however they may contain liquid or semi-solid components. In a particularly preferred embodiment, the dosage form is an orally administered system for delivering a pharmaceutical active ingredient to the gastro-intestinal tract of a human.

Suitable active ingredients for use in this invention include for example pharmaceuticals, minerals, vitamins and other nutraceuticals, oral care agents, flavorants and mixtures thereof. Suitable pharmaceuticals include analgesics, anti-inflammatory agents, antiarthritics, anesthetics, antihistamines, antitussives, antibiotics, anti-infective agents, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, decongestants, oral contraceptives, diuretics, expectorants, gastrointestinal agents, migraine preparations, motion sickness products, mucolytics, muscle relaxants, osteoporosis preparations, polydimethylsiloxanes, respiratory agents, sleep-aids, urinary tract agents and mixtures thereof.

Suitable oral care agents include breath fresheners, tooth whiteners, antimicrobial agents, tooth mineralizers, tooth decay inhibitors, topical anesthetics, mucoprotectants, and the like.

Suitable flavorants include menthol, peppermint, mint flavors, fruit flavors, chocolate, vanilla, bubblegum flavors, coffee flavors, liqueur flavors and combinations and the like.

Examples of suitable gastrointestinal agents include antacids such as calcium carbonate, magnesium hydroxide, magnesium oxide, magnesium carbonate, aluminum hydroxide, sodium bicarbonate, dihydroxyaluminum sodium carbonate; stimulant laxatives, such as bisacodyl, cascara sagrada, danthron, senna, phenolphthalein, aloe, castor oil, ricinoleic acid, and dehydrocholic acid, and mixtures thereof; H2 receptor antagonists, such as famotadine, ranitidine, cimetadine, nizatidine; proton pump inhibitors such as omeprazole or lansoprazole; gastrointestinal cytoprotectives, such as sucraflate and misoprostol; gastrointestinal prokinetics, such as prucalopride, antibiotics for *H. pylori*, such as clarithromycin, amoxicillin, tetracycline, and metronidazole; antidiarrheals, such as diphenoxylate and loperamide; glycopyrrolate; antiemetics, such as ondansetron, analgesics, such as mesalamine.

In one embodiment of the invention, the active ingredient may be selected from bisacodyl, famotadine, ranitidine, cimetidine, prucalopride, diphenoxylate, loperamide, lactase, mesalamine, bismuth, antacids, and pharmaceutically acceptable salts, esters, isomers, and mixtures thereof.

In another embodiment, the active ingredient is selected from analgesics, anti-inflammatories, and antipyretics, e.g. non-steroidal anti-inflammatory drugs (NSAIDs), including propionic acid derivatives, e.g. ibuprofen, naproxen, ketoprofen and the like; acetic acid derivatives, e.g. indomethacin, diclofenac, sulindac, tolmetin, and the like; fenamic acid derivatives, e.g. mefanamic acid, meclofenamic acid, flufenamic acid, and the like; biphenylcarbodylic acid derivatives, e.g. diflunisal, flufenisal, and the like; and oxicams, e.g. piroxicam, sudoxicam, isoxicam, meloxicam, and the like. In one particular embodiment, the active ingredient is selected from propionic acid derivative NSAID, e.g. ibuprofen, naproxen, flurbiprofen, fenbufen, fenoprofen, indoprofen, ketoprofen, fluprofen, pirprofen, carprofen, oxaprozin, pranoprofen, suprofen, and pharmaceutically acceptable salts, derivatives, and combinations thereof. In another particular embodiment of the invention, the active ingredient may be selected from acetaminophen, acetyl salicylic acid, ibuprofen, naproxen, ketoprofen, flurbiprofen, diclofenac, cyclobenzaprine, meloxicam, rofecoxib, celecoxib, and pharmaceutically acceptable salts, esters, isomers, and mixtures thereof.

In another embodiment of the invention, the active ingredient may be selected from upper respiratory agents, such as pseudoephedrine, phenylpropanolamine, chlorpheniramine, dextromethorphan, diphenhydramine, astemizole, terfenadine, fexofenadine, loratadine, desloratadine, cetirizine, mixtures thereof and pharmaceutically acceptable salts, esters, isomers, and mixtures thereof.

Examples of suitable polydimethylsiloxanes, which include, but are not limited to dimethicone and simethicone, are those disclosed in U.S. Pat. Nos. 4,906,478, 5,275,822, and 6,103,260, the contents of each is expressly incorporated herein by reference. As used herein, the term "simethicone" refers to the broader class of polydimethylsiloxanes, including but not limited to simethicone and dimethicone.

The active ingredient or ingredients are present in the dosage form in a therapeutically effective amount, which is an amount that produces the desired therapeutic response upon oral administration and can be readily determined by one skilled in the art. In determining such amounts, the particular active ingredient being administered, the bioavailability characteristics of the active ingredient, the dosing regimen, the age and weight of the patient, and other factors must be considered, as known in the art. Typically, the dosage form comprises at least about 1 weight percent, for example, the dosage form comprises at least about 5 weight percent, say at least about 20 weight percent of a combination of one or more active ingredients. In one embodiment, a core comprises a total of at least about 25 weight percent (based on the weight of the core) of one or more active ingredients.

The active ingredient or ingredients may be present in the dosage form in any form. For example, the active ingredient may be dispersed at the molecular level, e.g. melted or dissolved, within the dosage form, or may be in the form of particles, which in turn may be coated or uncoated. If an active ingredient is in the form of particles, the particles (whether coated or uncoated) typically have an average particle size of about 1-2000 microns. In one embodiment, such particles are crystals having an average particle size of about 1-300 microns. In another embodiment, the particles are granules or pellets having an average particle size of about 50-2000 microns, for example about 50-1000 microns, say about 100-800 microns. In certain embodiments in which one or more active ingredients are in the form of particles, the active ingredient particles are contained within one or more cores of the dosage form.

Each core may be any solid form. As used herein, "core" refers to a material which is at least partially enveloped or surrounded by another material. Preferably, a core is a self-contained unitary object, such as a tablet or capsule. Typically, a core comprises a solid, for example, a core may be a compressed or molded tablet, hard or soft capsule, suppository, or a confectionery form such as a lozenge, nougat, caramel, fondant, or fat based composition. In certain other embodiments, a core or a portion thereof may be in the form of a semi-solid or a liquid in the finished dosage form. For example a core may comprise a liquid filled capsule, or a semisolid fondant material. In embodiments in which a core comprises a flowable component, such as a plurality of granules or particles, or a liquid, the core preferably additionally comprises an enveloping component, such as a capsule shell, or a coating, for containing the flowable material. In certain particular embodiments in which a core comprises an enveloping component, the shell or shell portions of the present invention are in direct contact with the enveloping component of the core, which separates the shell from the flowable component of the core.

The dosage form comprises at least two cores, e.g. a first core and a second core. The dosage form may comprise more than two cores. The cores may have the same or different compositions, comprise the same or different active ingredients, excipients (inactive ingredients that may be useful for conferring desired physical properties to the dosage core), and the like. One or more cores may be substantially free of active ingredient. The cores may even comprise incompatible ingredients from one another.

Each core is completely surrounded by, or embedded in, the shell. A portion of the shell, referred herein as the "interior wall" separates the first and second cores. The distance between the first and second cores, i.e. thickness of the interior wall, may vary depending upon the desired release characteristics of the dosage form, or practical considerations related to the manufacturing process. In certain embodiments, the distance between the first and second cores within the dosage form, i.e. the thickness of the interior wall, is on the order of the thickness of the shell proximal to the core that is distal to the opening or openings. For example, the thickness of the interior wall may be from about 10% to about 200% of the thickness of a core.

Each core may have one of a variety of different shapes. Each core may have the same or different physical dimensions, shape, etc. as the other cores. For example the first and second cores may have different diameters or thicknesses. For example, a core may be shaped as a polyhedron, such as a cube, pyramid, prism, or the like; or may have the geometry of a space figure with some non-flat faces, such as a cone, truncated cone, cylinder, sphere, torus, or the like. In certain embodiments, a core has one or more major faces. For example, in embodiments wherein a core is a compressed tablet, the core surface typically has opposing upper and lower faces formed by contact with the upper and lower punch faces in the compression machine. In such embodiments the core surface typically further comprises a "belly-band" located between the upper and lower faces, and formed by contact with the die walls in the compression machine. A core may also comprise a multilayer tablet.

In one embodiment at least one core is a compressed tablet having a hardness from about 2 to about 30 kp/cm$^2$, e.g. from about 6 to about 25 kp/cm$^2$. "Hardness" is a term used in the art to describe the diametral breaking strength of either the core or the coated solid dosage form as measured by conventional pharmaceutical hardness testing equipment, such as a Schleuniger Hardness Tester. In order to compare values across different size tablets, the breaking strength must be normalized for the area of the break. This normalized value, expressed in kp/cm$^2$, is sometimes referred in the art as tablet tensile strength. A general discussion of tablet hardness testing is found in Leiberman et al., *Pharmaceutical Dosage Forms—Tablets*, Volume 2, 2$^{nd}$ ed., Marcel Dekker Inc., 1990, pp. 213-217, 327-329. In another embodiment, all the cores in the dosage form comprise a compressed tablet having a hardness from about 2 to about 30 kp/cm$^2$, e.g. from about 6 to about 25 kp/cm$^2$.

The first and second cores may be oriented side by side. For example, in the case of cores that are compressed tablets, their belly bands are adjacent to and in contact with the interior wall. See for example FIG. 1A, which depicts a cross-sectional view of a dosage form according to the invention comprising two side-by-side cores that are compressed tablets. Alternatively, the cores may be oriented one on top of the other such that their upper or lower faces are adjacent to and in contact with the interior wall. See for example, FIG. 5A, which shows a cross-sectional view of another dosage form according to the invention comprising "upper and lower" cores. The thickness of the shell may vary among various locations around the dosage form. For example, in embodiments where the cores have different sizes from one another, the shell may, as a result, have a smaller thickness around one core than the other. In embodiments where one or more cores have a different shape than that of the surrounding shell surface, the shell thickness will be different around certain portions of a core than around certain other portions. In embodiments where the shell comprises more than one portion, the shell portions may have different thickness from one another at corresponding locations. In embodiments where the cores are positioned asymmetrically within the dosage form, the shell thickness will vary accordingly. This may be exploited to adjust the relative onset or rate of release of active ingredient from the two cores. For example, active ingredient contained in a smaller core could be released after the release of active ingredient from a larger core has begun, due to the relative thinness of the shell around the larger core. In another example, active ingredient contained in a first, elongated, core could begin to be released sooner than active ingredient from a second, more symmetrically shaped core due to the relative thinness of the shell proximal to the elongated portion of the first core.

Exemplary core shapes that may be employed include tablet shapes formed from compression tooling shapes described by "The Elizabeth Companies Tablet Design Training Manual" (Elizabeth Carbide Die Co., Inc., p. 7 (McKeesport, Pa.) (incorporated herein by reference) as follows (the tablet shape corresponds inversely to the shape of the compression tooling):

| | |
|---|---|
| 1. | Shallow Concave. |
| 2. | Standard Concave. |
| 3. | Deep Concave. |
| 4. | Extra Deep Concave. |
| 5. | Modified Ball Concave. |
| 6. | Standard Concave Bisect. |
| 7. | Standard Concave Double Bisect. |
| 8. | Standard Concave European Bisect. |
| 9. | Standard Concave Partial Bisect. |
| 10. | Double Radius. |
| 11. | Bevel & Concave. |
| 12. | Flat Plain. |
| 13. | Flat-Faced-Beveled Edge (F.F.B.E.). |
| 14. | F.F.B.E. Bisect. |
| 15. | F.F.B.E. Double Bisect. |
| 16. | Ring. |
| 17. | Dimple. |
| 18. | Ellipse. |
| 19. | Oval. |
| 20. | Capsule. |
| 21. | Rectangle. |
| 22. | Square. |
| 23. | Triangle. |
| 24. | Hexagon. |
| 25. | Pentagon. |
| 26. | Octagon. |
| 27. | Diamond. |
| 28. | Arrowhead. |
| 29. | Bullet. |
| 30. | Shallow Concave. |
| 31. | Standard Concave. |
| 32. | Deep Concave. |
| 33. | Extra Deep Concave. |
| 34. | Modified Ball Concave. |
| 35. | Standard Concave Bisect. |
| 36. | Standard Concave Double Bisect. |
| 37. | Standard Concave European Bisect. |
| 38. | Standard Concave Partial Bisect. |
| 39. | Double Radius. |
| 40. | Bevel & Concave. |
| 41. | Flat Plain. |
| 42. | Flat-Faced-Beveled Edge (F.F.B.E.). |
| 43. | F.F.B.E. Bisect. |
| 44. | F.F.B.E. Double Bisect. |
| 45. | Ring. |
| 46. | Dimple. |
| 47. | Ellipse. |
| 48. | Oval. |
| 49. | Capsule. |
| 50. | Rectangle. |
| 51. | Square. |
| 52. | Triangle. |
| 53. | Hexagon. |
| 54. | Pentagon. |
| 55. | Octagon. |
| 56. | Diamond. |
| 57. | Arrowhead. |

-continued

| | |
|---|---|
| 58. | Bullet. |
| 59. | Barrel. |
| 60. | Half Moon. |
| 61. | Shield. |
| 62. | Heart. |
| 63. | Almond. |
| 64. | House/Home Plate. |
| 65. | Parallelogram. |
| 66. | Trapezoid. |
| 67. | FIG. 8/Bar Bell. |
| 68. | Bow Tie. |
| 69. | Uneven Triangle. |

The cores may be prepared by any suitable method, including for example compression or molding, and depending on the method by which they are made, typically comprise active ingredient and a variety of excipients. The cores may be prepared by the same or different methods. For example, a first core may be prepared by compression, and a second core may be prepared by molding, or both cores may be prepared by compression.

In embodiments in which one or more cores, or portions thereof are made by compression, suitable excipients include fillers, binders, disintegrants, lubricants, glidants, and the like, as known in the art. In embodiments in which a core is made by compression and additionally confers modified release of an active ingredient contained therein, such core preferably further comprises a release-modifying compressible excipient.

Suitable fillers for use in making a core or core portion by compression include water-soluble compressible carbohydrates such as sugars, which include dextrose, sucrose, maltose, and lactose, sugar-alcohols, which include mannitol, sorbitol, maltitol, xylitol, starch hydrolysates, which include dextrins, and maltodextrins, and the like, water insoluble plastically deforming materials such as microcrystalline cellulose or other cellulosic derivatives, water-insoluble brittle fracture materials such as dicalcium phosphate, tricalcium phosphate and the like and mixtures thereof.

Suitable binders for making a core or core portion by compression include dry binders such as polyvinyl pyrrolidone, hydroxypropylmethylcellulose, and the like; wet binders such as water-soluble polymers, including hydrocolloids such as acacia, alginates, agar, guar gum, locust bean, carrageenan, carboxymethylcellulose, tara, gum arabic, tragacanth, pectin, xanthan, gellan, gelatin, maltodextrin, galactomannan, pusstulan, laminarin, scleroglucan, inulin, whelan, rhamsan, zooglan, methylan, chitin, cyclodextrin, chitosan, polyvinyl pyrrolidone, cellulosics, sucrose, starches, and the like; and derivatives and mixtures thereof.

Suitable disintegrants for making a core or core portion by compression, include sodium starch glycolate, cross-linked polyvinylpyrrolidone, cross-linked carboxymethylcellulose, starches, microcrystalline cellulose, and the like.

Suitable lubricants for making a core or core portion by compression include long chain fatty acids and their salts, such as magnesium stearate and stearic acid, talc, glycerides and waxes.

Suitable glidants for making a core or core portion by compression, include colloidal silicon dioxide, and the like.

Suitable release-modifying excipients for making a core or core portion by compression include swellable erodible hydrophillic materials, insoluble edible materials, pH-dependent polymers, and the like Suitable swellable erodible hydrophilic materials for use as release-modifying excipients for making a core or core portion by compression include: water swellable cellulose derivatives, polyalkalene glycols, thermoplastic polyalkalene oxides, acrylic polymers, hydrocolloids, clays, gelling starches, and swelling cross-linked polymers, and derivitives, copolymers, and combinations thereof. Examples of suitable water swellable cellulose derivatives include sodium carboxymethylcellulose, cross-linked hydroxypropylcellulose, hydroxypropyl cellulose (HPC), hydroxypropylmethylcellulose (HPMC), hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, hydroxypropylethylcellulose. Examples of suitable polyalkalene glyclols include polyethylene glycol. Examples of suitable thermoplastic polyalkalene oxides include poly (ethylene oxide). Examples of suitable acrylic polymers include potassium methacrylate-divinylbenzene copolymer, polymethylmethacrylate, CARBOPOL (high-molceular weight cross-linked acrylic acid homopolymers and copolymers), and the like. Examples of suitable hydrocolloids include alginates, agar, guar gum, locust bean gum, kappa carrageenan, iota carrageenan, tara, gum arabic, tragacanth, pectin, xanthan gum, gellan gum, maltodextrin, galactomannan, pusstulan, laminarin, scleroglucan, gum arabic, inulin, pectin, gelatin, whelan, rhamsan, zooglan, methylan, chitin, cyclodextrin, chitosan. Examples of suitable clays include smectites such as bentonite, kaolin, and laponite; magnesium trisilicate, magnesium aluminum silicate, and the like, and derivatives and mixtures thereof. Examples of suitable gelling starches include acid hydrolyzed starches, swelling starches such as sodium starch glycolate, and derivatives thereof. Examples of suitable swelling cross-linked polymers include cross-linked polyvinyl pyrrolidone, cross-linked agar, and cross-linked carboxymethylcellose sodium.

Suitable insoluble edible materials for use as release-modifying excipients for making a core or core portion by compression include water-insoluble polymers, and low-melting hydrophobic materials. Examples of suitable water-insoluble polymers include ethylcellulose, polyvinyl alcohols, polyvinyl acetate, polycaprolactones, cellulose acetate and its derivatives, acrylates, methacrylates, acrylic acid copolymers; and the like and derivatives, copolymers, and combinations thereof. Suitable low-melting hydrophobic materials include fats, fatty acid esters, phospholipids, and waxes. Examples of suitable fats include hydrogenated vegetable oils such as for example cocoa butter, hydrogenated palm kernel oil, hydrogenated cottonseed oil, hydrogenated sunflower oil, and hydrogenated soybean oil; and free fatty acids and their salts. Examples of suitable fatty acid esters include sucrose fatty acid esters, mono, di, and triglycerides, glyceryl behenate, glyceryl palmitostearate, glyceryl monostearate, glyceryl tristearate, glyceryl trilaurylate, glyceryl myristate, Glyco-Wax-932, lauroyl macrogol-32 glycerides, and stearoyl macrogol-32 glycerides. Examples of suitable phospholipids include phosphotidyl choline, phosphotidyl serene, phosphotidyl enositol, and phosphotidic acid. Examples of suitable waxes include carnauba wax, spermaceti wax, beeswax, candelilla wax, shellac wax, microcrystalline wax, and paraffin wax; fat-containing mixtures such as chocolate; and the like.

Suitable pH-dependent polymers for use as release-modifying excipients for making a core or core portion by compression include enteric cellulose derivatives, for example hydroxypropyl methylcellulose phthalate, hydroxypropyl methylcellulose acetate succinate, cellulose acetate phthalate; natural resins such as shellac and zein; enteric acetate derivatives such as for example polyvinylacetate phthalate, cellulose acetate phthalate, acetaldehyde dimethylcellulose acetate; and enteric acrylate derivatives such as for example polymethacrylate-based polymers such as poly(methacrylic acid, methyl methacrylate) 1:2, which is commercially available from Rohm Pharma GmbH under the tradename EUDRAGIT S, and poly(methacrylic acid, methyl methacrylate) 1:1, which is commercially available from Rohm Pharma GmbH under the tradename EUDRAGIT L, and the like, and derivatives, salts, copolymers, and combinations thereof.

Suitable pharmaceutically acceptable adjuvants for making a core or core portion by compression include, preservatives; high intensity sweeteners such as aspartame, acesulfame potassium, sucralose, and saccharin; flavorants; colorants; antioxidants; surfactants; wetting agents; and the like and mixtures thereof.

In embodiments wherein one or more cores are prepared by compression, a dry blending (i.e. direct compression), or wet granulation process may be employed, as known in the art. In a dry blending (direct compression) method, the active ingredient or ingredients, together with the excipients, are blended in a suitable blender, than transferred directly to a compression machine for pressing into tablets. In a wet granulation method, the active ingredient or ingredients, appropriate excipients, and a solution or dispersion of a wet binder (e.g. an aqueous cooked starch paste, or solution of polyvinyl pyrrolidone) are mixed and granulated. Alternatively a dry binder may be included among the excipients, and the mixture may be granulated with water or other suitable solvent. Suitable apparatuses for wet granulation are known in the art, including low shear, e.g. planetary mixers; high shear mixers; and fluid beds, including rotary fluid beds. The resulting granulated material is dried, and optionally dry-blended with further ingredients, e.g. adjuvants and/or excipients such as for example lubricants, colorants, and the like. The final dry blend is then suitable for compression. Methods for direct compression and wet granulation processes are known in the art, and are described in detail in, for example, Lachman, et al., *The Theory and Practice of Industrial Pharmacy*, Chapter 11 (3rd ed. 1986).

The dry-blended, or wet granulated, powder mixture is typically compacted into tablets using a rotary compression machine as known in the art, such as for example those commercially available from Fette America Inc., Rockaway, N.J., or Manesty Machines LTD, Liverpool, UK. In a rotary compression machine, a metered volume of powder is filled into a die cavity, which rotates as part of a "die table" from the filling position to a compaction position where the powder is compacted between an upper and a lower punch to an ejection position where the resulting tablet is pushed from the die cavity by the lower punch and guided to an ejection chute by a stationary "take-off" bar.

Figure 6:
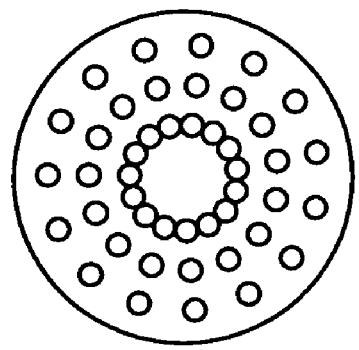
FIG. 6 shows various openings according to the invention.
Figure 6:
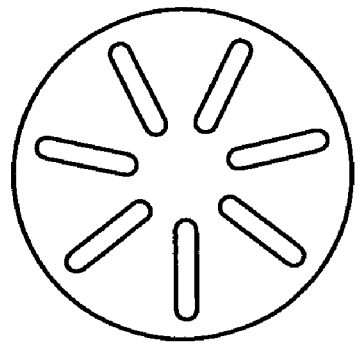
Figure 6:
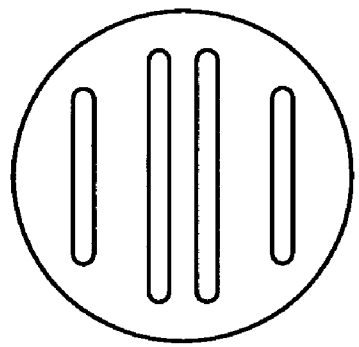
Figure 6:
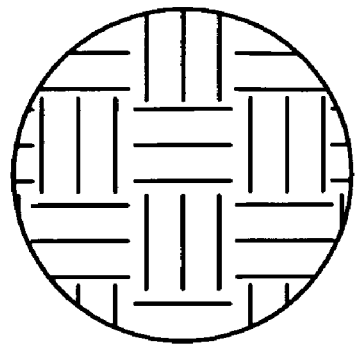

In one embodiment, at least one core is prepared by the compression methods and apparatus described in copending U.S. patent application Ser. No. 09/966,509, pages 16-27, the disclosure of which is incorporated herein by reference. Specifically, the core is made using a rotary compression module comprising a fill zone, compression zone, and ejection zone in a single apparatus having a double row die construction as shown in FIG. 6 of U.S. patent application Ser. No. 09/966, 509. The dies of the compression module are preferably filled using the assistance of a vacuum, with filters located in or near each die.

Cores made by compression may be single or multi-layer, for example bi-layer, tablets.

A shell surrounds the cores. The shell is continuous and completely surrounds the cores. The shell may be a single, unitary coating, or the shell may comprise multiple portions, e.g. a first shell portion and a second shell portion. In certain embodiments the shell or shell portions are in direct contact with a core or core portion. In certain other embodiments, the shell or shell portions are in direct contact with a subcoating or enveloping component which substantially surrounds a core or core portion. In embodiments in which the shell comprises a first and second shell portion, at least a first shell portion comprises openings therein. In embodiments, in which multiple shell portions are employed, the shell portions may have the same or different compositions and shapes from one another.

In certain embodiments the dosage form comprises a first shell portion and a second shell portion that are compositionally different. As used herein, the term "compositionally different" means having features that are readily distinguishable by qualitative or quantitative chemical analysis, physical testing, or visual observation. For example, the first and second shell portions may contain different ingredients, or different levels of the same ingredients, or the first and second shell portions may have different physical or chemical properties, different functional properties, or be visually distinct. Examples of physical or chemical properties that may be different include hydrophylicity, hydrophobicity, hygroscopicity, elasticity, plasticity, tensile strength, crystallinity, and density. Examples of functional properties which may be different include rate and/or extent of dissolution of the material itself or of an active ingredient therefrom, rate of disintegration of the material, permeability to active ingredients, permeability to water or aqueous media, and the like. Examples of visual distinctions include size, shape, topography, or other geometric features, color, hue, opacity, and gloss.

In one embodiment, the first core is surrounded by a first shell portion, and the second core is surrounded by a second shell portion. For example, in one particular such embodiment, the first and second cores may contain the same active ingredient in the same amount, and may be essentially identical in size, shape, and composition, while the first and second shell portions are have different dissolution properties, and confer different release profiles to the active ingredient portions contained in the first and second cores.

In another embodiment, the first and second cores are oriented side by side, for example as two compressed tablets with their belly bands adjacent to and in contact with the interior wall. The upper faces of both cores may be in contact with a first shell portion, and the lower faces of both cores may be in contact with a second shell portion. In certain other embodiments in which the first and second cores are compressed or molded tablets oriented one on top of the other such that their upper or lower faces are adjacent to and in contact with the interior wall, one core may be entirely surrounded by a first shell portion, and the other core may be entirely surrounded by a second shell portion.

In one embodiment, the surface of the first or second core is substantially totally coated with a subcoating. In this embodiment, a shell comprising first and second shell portions is in direct contact with the surface of the subcoating. As used herein, "substantially totally covering" means at least about 95 percent of the surface area of the core is covered by the subcoating.

The use of subcoatings is well known in the art and disclosed in, for example, U.S. Pat. Nos. 3,185,626, which is incorporated by reference herein. Any composition suitable for film-coating a tablet may be used as a subcoating according to the present invention. Examples of suitable subcoatings are disclosed in U.S. Pat. Nos. 4,683,256, 4,543,370, 4,643, 894, 4,828,841, 4,725,441, 4,802,924, 5,630,871, and 6,274, 162, which are all incorporated by reference herein. Additional suitable subcoatings include one or more of the following ingredients: cellulose ethers such as hydroxypropylmethylcellulose, hydroxypropylcellulose, and hydroxyethylcellulose; polycarbohydrates such as xanthan gum, starch, and maltodextrin; plasticizers including for example, glycerin, polyethylene glycol, propylene glycol, dibutyl sebecate, triethyl citrate, vegetable oils such as castor oil, surfactants such as polysorbate-80, sodium lauryl sulfate and dioctyl-sodium sulfosuccinate; polycarbohydrates, pigments, and opacifiers.

In one embodiment, the subcoating comprises, based upon the total weight of the subcoating, from about 2 percent to about 8 percent, e.g. from about 4 percent to about 6 percent of a water-soluble cellulose ether and from about 0.1 percent to about 1 percent, castor oil, as disclosed in detail in U.S. Pat. No. 5,658,589, which is incorporated by reference herein. In another embodiment, the subcoating comprises, based upon the total weight of the subcoating, from about 20 percent to about 50 percent, e.g., from about 25 percent to about 40 percent of HPMC; from about 45 percent to about 75 percent, e.g., from about 50 percent to about 70 percent of maltodextrin; and from about 1 percent to about 10 percent, e.g., from about 5 percent to about 10 percent of PEG 400.

In embodiments in which a subcoating is employed, the dried subcoating typically is present in an amount, based upon the dry weight of the core, from about 0 percent to about 5 percent.

In another embodiment, one or more cores, e.g. all the cores, are substantially free of subcoating, and the shell or a shell portion is in direct contact with a core surface.

The shell comprises one or more openings therein. The openings provide a passageway for communication between at least one core, or portion thereof, and the exterior of the dosage form. One or more openings may extend completely through the thickness of the shell, or only partially through the shell. In a preferred embodiment, the shell comprises a plurality of openings. In either case, at least one core in the dosage form is distal to the opening or openings. That is, at least one core does not communicate with the exterior of the dosage form through such an opening in the shell.

Preferably, the opening or openings are proximal to at least one core. Accordingly, in one embodiment, at least one core is distal to the opening or openings and at least one core is proximal to the opening or openings. The opening or openings are preferably in contact with one or more cores.

Figure 1B:
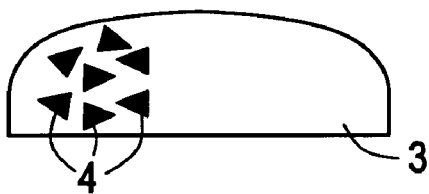

FIG. 1A depicts a cross-section of a dosage form according to the invention comprising first and second, side-by-side cores 1, 2 that are compressed tablets. The cores are surrounded by a shell 3. Shell 3 comprises a plurality of openings 4 in the shape of triangles. Openings 4 are distal to core 1 and proximal to core 2. In particular, openings 4 contact core 2. FIG. 1B shows a top view of the dosage form of FIG. 1A.

Figure 2A:
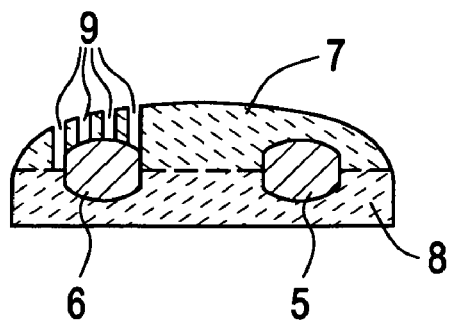
FIGS. 2A, 2B, and 2C depict another dosage form according to the invention.
Figure 2B:
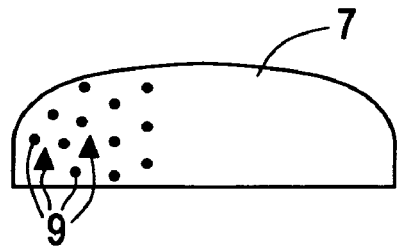
Figure 2C:
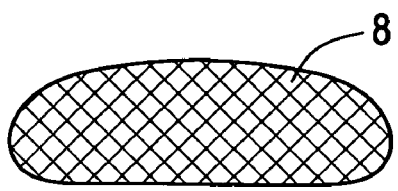

FIG. 2A depicts a cross-section of another dosage form according to the invention. This dosage form comprises first and second, side-by-side cores 5, 6 surrounded by a shell having two shell portions 7, 8. Shell portion 7 comprises a plurality of openings 9, which are distal to core 5 and proximal to and contacting core 6. FIG. 2B shows a top view of the dosage form of FIG. 2A, showing openings 9 in shell portion 7. Openings 9 are shaped as triangles and circles. FIG. 2C is a bottom view of the dosage form of FIG. 2A, showing shell portion 8.

Figure 3A:
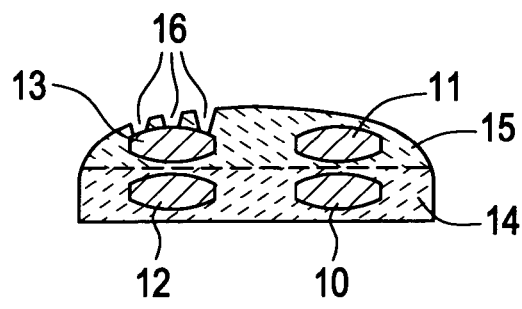
FIGS. 3A, 3B, and 3C depict another dosage form according to the invention.
Figure 3B:
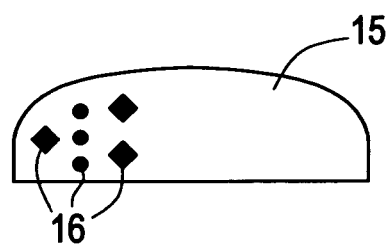
Figure 3C:

FIG. 3A depicts a cross-sectional view of another dosage form according to the invention. The dosage form comprises four cores 10, 11, 12, and 13, which are surrounded by a shell having two shell portions 14, 15. Cores 11 and 13 reside within shell portion 15, while cores 10 and 12 reside in shell portion 14. Shell portion 15 comprises a plurality of openings 16, which are distal to cores 10, 11 and 12, and proximal to only core 13. Openings 16 contact core 13. FIG. 3B is a top view of the dosage form of FIG. 3A, showing openings 16 in shell portion 15. FIG. 3C is a bottom view of the dosage form of FIG. 3A, showing shell portion 14.

Figure 4A:
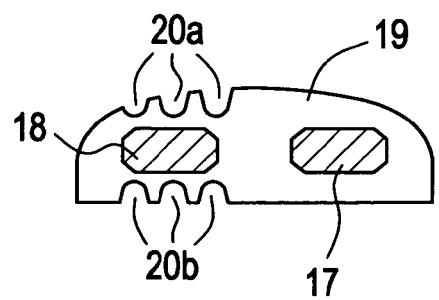
FIGS. 4A, 4B, and 4C, depict another dosage form according to the invention.
Figure 4B:
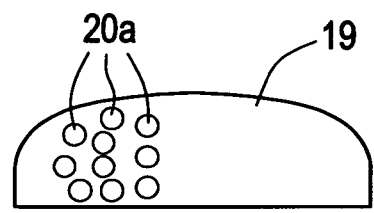
Figure 4C:
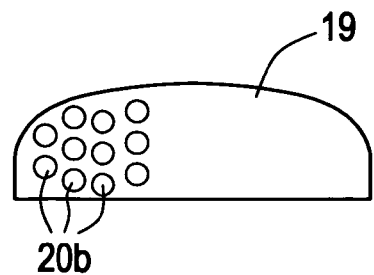

FIG. 4A depicts a cross-sectional view of another dosage form according to the invention. The dosage form comprises two cores 17, 18 surrounded by shell 19. Shell 19 comprises a plurality of openings 20a, 20b. Openings 20a, 20b are distal to core 17 and proximal to, but not contacting, core 18. In this example, openings 20a, 20b extend only partially through the shell, and do not contact core 18. FIG. 4B is a top view of the dosage form of FIG. 4A, showing openings 20a. FIG. 4C is a bottom view of the dosage form of FIG. 4A, showing openings 20b.

In embodiments such as those depicted in FIG. 4, in which one or more openings extend only partially through the shell, and do not contact a core, the openings may be in the form of dimples or surface cavities, e.g. debossments or intagliations. These partial openings may grow into complete passageways in contact with a core at some time after exposure of the dosage form to a suitable liquid medium, such as for example in-vitro dissolution testing media, or gastro-intestinal fluids.

Figure 5A:
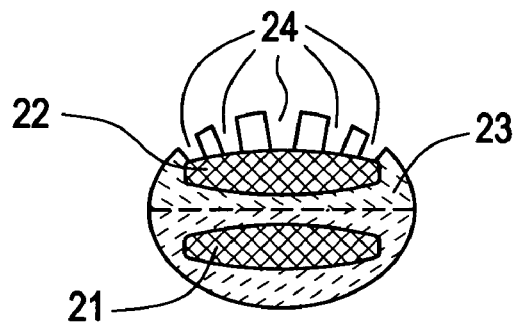
FIGS. 5A, 5B, and 5C depict another dosage form according to the invention.
Figure 5B:
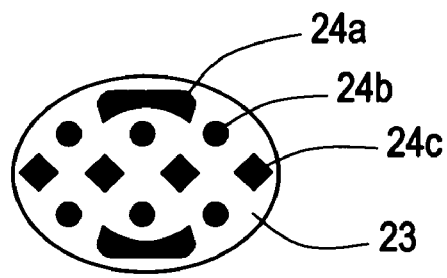
Figure 5C:
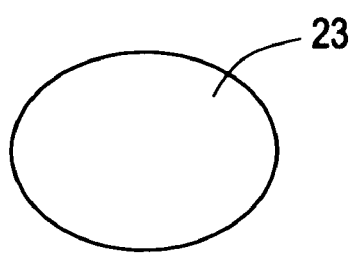

FIG. 5A is a cross-sectional view of another dosage form according to the invention. The dosage form comprises first and second cores 21, 22 disposed one on top of another. Shell 23 surrounds cores 21, 22 and contains openings 24 that are distal to core 21 and proximal to and contacting core 22. FIG. 5B is a top view of the dosage form of FIG. 5A, showing openings 24, which have three different shapes 24a, 24b, and 24c. FIG. 5C is a bottom view of the dosage form of FIG. 5A.

Each opening may have dimensions, e.g. length, width, or diameter, in the range of about 0.1% to about 100%, of the diameter of the dosage form, or of any dimension (e.g. diameter, length, or width) of a major face of the dosage form. The diameter or width of each opening is preferably from about 0.5% to about 5% of the diameter of the dosage form, or of any dimension (e.g. diameter, length, or width) of a major face of the dosage form. In certain embodiments the diameter or width of the openings may range from about 200 to about 2000 microns. The length of the openings may range from about 1% to about 100% of the diameter or width of the dosage form, or of the diameter or width of a major face of the dosage form. In certain particular embodiments, the diameter or width of a major face of the dosage form is from about 10,000 to about 20,000 microns. In one particular embodiment, the length of the openings is from about 100 to about 20,000 microns. The depth of the openings is typically from about 75% to about 100% of the thickness of the shell at the location of the openings. In certain embodiments, the thickness of the shell at the location of the openings typically ranges from about 20 to about 800 microns, e.g. from about 100 to about 400 microns. In one particular embodiment, the depth of the openings is from about 75 to about 400 microns. If a plurality of openings are present, they are typically spaced from one another by at least about one half, e.g. at least about one, times the smallest dimension of the smallest opening. The openings may have a variety of shapes, or be arranged in a variety of different patterns, and may have similar or different sizes, such as depicted in FIG. 6.

In one embodiment, the size of the openings is small enough to prevent the core proximal thereto from being tasted, yet the number of openings is large enough to provide communication between a certain percentage of surface area of such proximal core and the exterior of the dosage form.

The dosage forms of the invention provide modified release of one or more active ingredients contained therein. The active ingredient or ingredients may be found within one or more cores, the shell, or portions or combinations thereof. Preferably, one or more active ingredients are contained in one or more cores. More preferably, at least one active ingredient is contained in each of the first and second cores.

Modified release of at least one active ingredient in the dosage form is provided by the shell, or a portion thereof. As used herein, the term "modified release" means the release of an active ingredient from a dosage form or a portion thereof in other than an immediate release fashion, i.e., other than immediately upon contact of the dosage form or portion thereof with a liquid medium. As known in the art, types of modified release include delayed or controlled. Types of controlled release include prolonged, sustained, extended, retarded, and the like. Modified release profiles that incorporate a delayed release feature include pulsatile, repeat action, and the like. As is also known in the art, suitable mechanisms for achieving modified release of an active ingredient include diffusion, erosion, surface area control via geometry and/or impermeable barriers, and other known mechanisms known.

In a preferred embodiment, at least one active ingredient is released from the first (proximal) core in an immediate release fashion. As used herein, "immediate release" means the dissolution characteristics of an active ingredient meets USP specifications for immediate release tablets containing the active ingredient. For example, for acetaminophen tablets, USP 24 specifies that in pH 5.8 phosphate buffer, using USP apparatus 2 (paddles) at 50 rpm, at least 80% of the acetaminophen contained in the dosage form is released therefrom within 30 minutes after dosing, and for ibuprofen tablets, USP 24 specifies that in pH 7.2 phosphate buffer, using USP apparatus 2 (paddles) at 50 rpm, at least 80% of the ibuprofen contained in the dosage form is released therefrom within 60 minutes after dosing. See USP 24, 2000 Version, 19-20 and 856 (1999).

The composition of the shell may function to modify the release therethrough of an active ingredient contained in an underlying core. In one embodiment, the shell may function to delay release of an active ingredient from an underlying core. In another embodiment, the shell may function to sustain, extend, retard, or prolong the release of at least one active ingredient from the second (distally located) core.

In one embodiment, the shell comprises a release modifying moldable excipient, such as, but not limited to, swellable erodible hydrophilic materials, pH-dependent polymers, pore formers, and insoluble edible materials.

In one embodiment, the release-modifying moldable excipient is selected from hydroxypropylmethylcellulose, polyethylene oxide, ammonio methacrylate copolymer type B, and shellac, and combinations thereof.

Suitable swellable erodible hydrophilic materials for use as release modifying moldable excipients include water swellable cellulose derivatives, polyalkalene glycols, thermoplastic polyalkalene oxides, acrylic polymers, hydrocolloids, clays, gelling starches, and swelling cross-linked polymers, and derivitives, copolymers, and combinations thereof. Examples of suitable water swellable cellulose derivatives include sodium carboxymethylcellulose, cross-linked hydroxypropylcellulose, hydroxypropyl cellulose (HPC), hydroxypropylmethylcellulose (HPMC), hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, hydroxypropylethylcellulose. Examples of suitable polyalkalene glyclols include polyethylene glycol. Examples of suitable thermoplastic polyalkalene oxides include poly (ethylene oxide). Examples of suitable acrylic polymers include potassium methacrylatedivinylbenzene copolymer, polymethylmethacrylate, CARBOPOL (high-molceular weight cross-linked acrylic acid homopolymers and copolymers), and the like. Examples of suitable hydrocolloids include alginates, agar, guar gum, locust bean gum, kappa carrageenan, iota carrageenan, tara, gum arabic, tragacanth, pectin, xanthan gum, gellan gum, maltodextrin, galactomannan, pusstulan, laminarin, scleroglucan, gum arabic, inulin, pectin, gelatin, whelan, rhamsan, zooglan, methylan, chitin, cyclodextrin, chitosan. Examples of suitable clays include smectites such as bentonite, kaolin, and laponite; magnesium trisilicate, magnesium aluminum silicate, and the like, and derivatives and mixtures thereof. Examples of suitable gelling starches include acid hydrolyzed starches, swelling starches such as sodium starch glycolate, and derivatives thereof. Examples of suitable swelling cross-linked polymers include cross-linked polyvinyl pyrrolidone, cross-linked agar, and cross-linked carboxymethylcellulose sodium.

Suitable pH-dependent polymers for use as release-modifying moldable excipients include enteric cellulose derivatives, for example hydroxypropyl methylcellulose phthalate, hydroxypropyl methylcellulose acetate succinate, cellulose acetate phthalate; natural resins such as shellac and zein; enteric acetate derivatives such as for example polyvinylacetate phthalate, cellulose acetate phthalate, acetaldehyde dimethylcellulose acetate; and enteric acrylate derivatives such as for example polymethacrylate-based polymers such as poly(methacrylic acid, methyl methacrylate) 1:2, which is commercially available from Rohm Pharma GmbH under the tradename EUDRAGIT S, and poly(methacrylic acid, methyl methacrylate) 1:1, which is commercially available from Rohm Pharma GmbH under the tradename EUDRAGIT L, and the like, and derivatives, salts, copolymers, and combinations thereof.

Suitable insoluble edible materials for use as release-modifying moldable excipients include water-insoluble polymers, and low-melting hydrophobic materials. Examples of suitable water-insoluble polymers include ethylcellulose, polyvinyl alcohols, polyvinyl acetate, polycaprolactones, cellulose acetate and its derivatives, acrylates, methacrylates, acrylic acid copolymers; and the like and derivatives, copolymers, and combinations thereof. Suitable low-melting hydrophobic materials include fats, fatty acid esters, phospholipids, and waxes. Examples of suitable fats include hydrogenated vegetable oils such as for example cocoa butter, hydrogenated palm kernel oil, hydrogenated cottonseed oil, hydrogenated sunflower oil, and hydrogenated soybean oil; and free fatty acids and their salts. Examples of suitable fatty acid esters include sucrose fatty acid esters, mono, di, and triglycerides, glyceryl behenate, glyceryl palmitostearate, glyceryl monostearate, glyceryl tristearate, glyceryl trilaurylate, glyceryl myristate, GlycoWax-932, lauroyl macrogol-32 glycerides, and stearoyl macrogol-32 glycerides. Examples of suitable phospholipids include phosphotidyl choline, phosphotidyl serene, phosphotidyl enositol, and phosphotidic acid. Examples of suitable waxes include carnauba wax, spermaceti wax, beeswax, candelilla wax, shellac wax, microcrystalline wax, and paraffin wax; fat-containing mixtures such as chocolate; and the like.

Suitable pore formers for use as release-modifying moldable excipients include water-soluble organic and inorganic materials. In one embodiment the pore former is hydroxypropylmethylcellulose. Examples of suitable water-soluble organic materials include water soluble polymers including water soluble cellulose derivatives such as hydroxypropylmethylcellulose, and hydroxypropylcellulose; water soluble carbohydrates such as sugars, and starches; water soluble polymers such as polyvinylpyrrolidone and polyethylene glycol, and insoluble swelling polymers such as microcrystalline cellulose. Examples of suitable water soluble inorganic materials include salts such as sodium chloride and potassium chloride and the like and/or mixtures thereof.

In another embodiment, the dosage form is substantially free (i.e. less than 1% by weight, preferably less than about 0.1% by weight, based upon the shell weight) of charge control agents. As used herein, the term "charge control agents" refers to a material having a charge control function, such as those used for electrostatic deposition of coatings onto substrates. Such charge control agents include metal salicylates, for example zinc salicylate, magnesium salicylate and calcium salicylate; quaternary ammonium salts; benzalkonium chloride; benzethonium chloride; trimethyl tetradecyl ammonium bromide (cetrimide); and cyclodextrins and their adducts.

Accordingly, in certain embodiments, the dosage form comprises at least two cores containing the same or different active ingredient surrounded by a shell comprising a release modifying moldable excipient. The shell also comprises one or more openings proximal to a first core but distal to a second core. In this manner, the first core communicates with the exterior of the dosage form through the openings, but the second core does not. Upon contact of the dosage form with a suitable liquid medium, e.g. in-vitro dissolution media or gastro-intestinal fluids, the liquid medium contacts the first core via the openings, and active ingredient contained in the first core is promptly, preferably immediately, released from the dosage form. Liquid media cannot, however, initially contact active ingredient contained in the second core. Release of active ingredient contained in the second core is therefore dependent on the nature of the shell. This active ingredient is released from the dosage form in a modified manner.

In a first preferred embodiment such as described in the preceding paragraph, a time delay, or lag time precedes release of active ingredient contained in the second core. Particularly useful lag times include those of at least about 1 hour, e.g. at least about 4 hours, say at least about 6 hours. In one such embodiment, active ingredient contained in the second core may be released promptly or substantially immediately following the lag time, as a delayed burst. In certain such embodiments wherein separate doses of the same active ingredient are contained in the first and second cores, that particular active ingredient is said to be released from the dosage form in a pulsatile manner. In another such embodiment, active ingredient contained in the second core may be released in a controlled, sustained, prolonged, or extended manner following the lag time.

In a second preferred embodiment such as described in the preceding paragraphs, one or more active ingredients contained in the second core are released in a controlled, sustained, prolonged, or extended manner beginning initially upon contact of the dosage for with a liquid medium, without a substantial preceding lag time, e.g. release of at least one active ingredients begins within 30 minutes, e.g. within 15 minutes, say within 10 minutes, of contact of the dosage form with a liquid medium.

In certain embodiments, the shell itself, e.g. a portion thereof, or an outer coating thereon may also contain active ingredient. In one embodiment, such active ingredient will be released immediately from the dosage form upon ingestion, or contacting of the dosage form with a liquid medium. In another embodiment, such active ingredient will be released in a controlled, sustained, prolonged, or extended fashion upon ingestion, or contacting of the dosage form with a liquid medium.

In certain preferred embodiments of the invention, the cores, the shell, any portions thereof, or both are prepared by molding. In particular, the cores, the shell, or both may be made by solvent-based molding or solvent-free molding. In such embodiments, the core or the shell is made from a flowable material optionally comprising active ingredient. The flowable material may be any edible material that is flowable at a temperature between about 37° C. and 250° C., and that is solid, semi-solid, or can form a gel at a temperature between about −10° C. and about 35° C. When it is in the fluid or flowable state, the flowable material may comprise a dissolved or molten component for solvent-free molding, or optionally a solvent such as for example water or organic solvents, or combinations thereof, for solvent-based molding. The solvent may be partially or substantially removed by drying.

In one embodiment, solvent-based or solvent-free molding is performed via thermal setting molding using the method and apparatus described in copending U.S. patent application Ser. No. 09/966,450, pages 57-63, the disclosure of which is incorporated herein by reference. In this embodiment, a core or shell is formed by injecting flowable form into a molding chamber. The flowable material preferably comprises a thermal setting material at a temperature above its melting point but below the decomposition temperature of any active ingredient contained therein. The flowable material is cooled and solidifies in the molding chamber into a shaped form (i.e., having the shape of the mold).

According to this method, the flowable material may comprise solid particles suspended in a molten matrix, for example a polymer matrix. The flowable material may be completely molten or in the form of a paste. The flowable material may comprise an active ingredient dissolved in a molten material in the case of solvent-free molding. Alternatively, the flowable material may be made by dissolving a solid in a solvent, which solvent is then evaporated after the molding step in the case of solvent-based molding.

In another embodiment, solvent-based or solvent-free molding is performed by thermal cycle molding using the method and apparatus described in copending U.S. patent application Ser. No. 09/966,497, pages 27-51, the disclosure of which is incorporated herein by reference. Thermal cycle molding is performed by injecting a flowable material into a heated molding chamber. The flowable material may comprise active ingredient and a thermoplastic material at a temperature above the set temperature of the thermoplastic material but below the decomposition temperature of active ingredient. The flowable material is cooled and solidifies in the molding chamber into a shaped form (i.e., having the shape of the mold).

In the thermal cycle molding method and apparatus of U.S. patent application Ser. No. 09/966,497 a thermal cycle molding module having the general configuration shown in FIG. 3 therein is employed. The thermal cycle molding module 200 comprises a rotor 202 around which a plurality of mold units 204 are disposed. The thermal cycle molding module includes a reservoir 206 (see FIG. 4) for holding flowable material to make the core. In addition, the thermal cycle molding module is provided with a temperature control system for rapidly heating and cooling the mold units. FIGS. 55 and 56 depict the temperature control system 600.

The mold units may comprise center mold assemblies 212, upper mold assemblies 214, and lower mold assemblies 210, as shown in FIGS. 26-28, which mate to form mold cavities having a desired shape, for instance of a core or a shell surrounding one or more cores. As rotor 202 rotates, opposing center and upper mold assemblies or opposing center and lower mold assemblies close. Flowable material, which is heated to a flowable state in reservoir 206, is injected into the resulting mold cavities. The temperature of the flowable material is then decreased, hardening the flowable material. The mold assemblies open and eject the finished product.

In a particularly preferred embodiment of the invention, the shell is applied to the dosage form using a thermal cycle molding apparatus of the general type shown in FIGS. 28A-C of copending U.S. application Ser. No. 09/966,497 comprising rotatable center mold assemblies 212, lower mold assemblies 210 and upper mold assemblies 214. Cores are continuously fed to the mold assemblies. Shell flowable material, which is heated to a flowable state in reservoir 206, is injected into the mold cavities created by the closed mold assemblies holding the cores. The temperature of the shell flowable material is then decreased, hardening it around the cores. The mold assemblies open and eject the finished dosage forms. Shell coating is performed in two steps, each half of the dosage forms being coated separately as shown in the flow diagram of FIG. 28B of copending U.S. application Ser. No. 09/966,939 via rotation of the center mold assembly.

In particular, the mold assemblies for applying the shell are provided with two or more cavities to accommodate the desired number of cores in the dosage form. The cavities are separated by a wall, preferably made of rubber or metal, and the overall shape of the cavities conform to the shape of the cores.

In addition, the inside surface of at least one of the mold assemblies comprises one or more protrusions. Each protrusion, which is adjusted for shape and size as desired, masks a small location on an underlying core, leaving behind an opening in the shell at the site of the protrusion. The mold assemblies may comprise a plurality of protrusions to form a plurality of corresponding openings in the shell. In such case, the protrusions are located within the mold assemblies such that the resulting openings will be distal to at least one underlying core. For example, the protrusions may be located on the inside surface of only one mold assembly, say the upper mold assembly, or located within only a portion, i.e., one quadrant of the inside surface of one mold assembly.

In one embodiment, the compression module of copending U.S. patent application Ser. No. 09/966,509, pp. 16-27 may be employed to make cores. The shell may be made applied to these cores using a thermal cycle molding module as described above. A transfer device as described in U.S. patent application Ser. No. 09/966,414, pp. 51-57, the disclosure of which is incorporated herein by reference, may be used to transfer the cores from the compression module to the thermal cycle molding module. Such a transfer device may have the structure shown as 300 in FIG. 3 of copending U.S. application Ser. No. 09/966,939. It comprises a plurality of transfer units 304 attached in cantilever fashion to a belt 312 as shown in FIGS. 68 and 69 of copending U.S. application Ser. No. 09/966,939. The transfer device rotates and operates in sync with the compression module and the thermal cycle molding module to which it is coupled. Transfer units 304 comprise retainers 330 for holding cores as they travel around the transfer device.

Each transfer unit comprises multiple retainers for holding multiple cores side by side. In one embodiment, the between the retainers within each transfer unit is adjusted via a cam track/cam follower mechanism as the transfer units move around the transfer device. On arrival at the thermal cycle molding module, the cores grouped together for placement in a single dosage form, which have been held within a single transfer unit, are properly spaced from one another and ready to be fed into the mold assemblies. The cores may or may not have the same composition, as desired. The cores may comprise a single layer or multiple layers.

Alternatively, if cores of the same composition are to be used in the dosage forms, the compression module may be equipped with multi-tip compression tooling. Four-tip tooling, for example, may be used to make four cores within one die. The cores may comprise a single layer of multiple layers.

Suitable thermoplastic materials for use in or as the flowable material include both water soluble and water insoluble polymers that are generally linear, not crosslinked, and not strongly hydrogen bonded to adjacent polymer chains. Examples of suitable thermoplastic materials include: thermoplastic water swellable cellulose derivatives, thermoplastic water insoluble cellulose derivatrives, thermoplastic vinyl polymers, thermoplastic starches, thermplastic polyalkalene glycols, thermoplastic polyalkalene oxides, and amorphous sugar-glass, and the like, and derivatives, copolymers, and combinations thereof. Examples of suitable thermoplastic water swellable cellulose derivatives include hydroxypropyl cellulose (HPC), hydroxypropylmethyl cellulose (HPMC), methyl cellulose (MC). Examples of suitable thermoplastic water insoluble cellulose derivatrives include cellulose acetate (CA), ethyl cellulose (EC), cellulose acetate butyrate (CAB), cellulose propionate. Examples of suitable thermoplastic vinyl polymers include polyvinyl alcohol (PVA) and polyvinyl pyrrolidone (PVP). Examples of suitable thermoplastic starches are disclosed for example in U.S. Pat. No. 5,427,614.

Examples of suitable thermoplastic polyalkalene glycols include polyethylene glycol. Examples of suitable thermoplastic polyalkalene oxides include polyethylene oxide having a molecular weight from about 100,000 to about 900,000 Daltons. Other suitable thermoplastic materials include sugar in the form on an amorphous glass such as that used to make hard candy forms.

Any film former known in the art is suitable for use in the flowable material. Examples of suitable film formers include, but are not limited to, film-forming water soluble polymers, film-forming proteins, film-forming water insoluble polymers, and film-forming pH-dependent polymers. In one embodiment, the film-former for making the core or shell or portion thereof by molding may be selected from cellulose acetate, ammonio methacrylate copolymer type B, shellac, hydroxypropylmethylcellulose, and polyethylene oxide, and combinations thereof.

Suitable film-forming water soluble polymers include water soluble vinyl polymers such as polyvinylalcohol (PVA); water soluble polycarbohydrates such as hydroxypropyl starch, hydroxyethyl starch, pullulan, methylethyl starch, carboxymethyl starch, pre-gelatinized starches, and film-forming modified starches; water swellable cellulose derivatives such as hydroxypropyl cellulose (HPC), hydroxypropylmethyl cellulose (HPMC), methyl cellulose (MC), hydroxyethylmethylcellulose (HEMC), hydroxybutylmethylcellulose (HBMC), hydroxyethylethylcellulose (HEEC), and hydroxyethylhydroxypropylmethyl cellulose (HEMPMC); water soluble copolymers such as methacrylic acid and methacrylate ester copolymers, polyvinyl alcohol and polyethylene glycol copolymers, polyethylene oxide and polyvinylpyrrolidone copolymers; and derivatives and combinations thereof.

Suitable film-forming proteins may be natural or chemically modified, and include gelatin, whey protein, myofibrillar proteins, coaggulatable proteins such as albumin, casein, caseinates and casein isolates, soy protein and soy protein isolates, zein; and polymers, derivatives and mixtures thereof.

Suitable film-forming water insoluble polymers, include for example ethylcellulose, polyvinyl alcohols, polyvinyl acetate, polycaprolactones, cellulose acetate and its derivatives, acrylates, methacrylates, acrylic acid copolymers; and the like and derivatives, copolymers, and combinations thereof.

Suitable film-forming pH-dependent polymers include enteric cellulose derivatives, such as for example hydroxypropyl methylcellulose phthalate, hydroxypropyl methylcellulose acetate succinate, cellulose acetate phthalate; natural resins, such as shellac and zein; enteric acetate derivatives such as for example polyvinylacetate phthalate, cellulose acetate phthalate, acetaldehyde dimethylcellulose acetate; and enteric acrylate derivatives such as for example polymethacrylate-based polymers such as poly(methacrylic acid, methyl methacrylate) 1:2, which is commercially available from Rohm Pharma GmbH under the tradename, EUDRAGIT S, and poly(methacrylic acid, methyl methacrylate) 1:1, which is commercially available from Rohm Pharma GmbH under the tradename, EUDRAGIT L, and the like, and derivatives, salts, copolymers, and combinations thereof.

One suitable hydroxypropylmethylcellulose compound for use as a thermoplastic film-forming water soluble polymer is "HPMC 2910", which is a cellulose ether having a degree of substitution of about 1.9 and a hydroxypropyl molar substitution of 0.23, and containing, based upon the total weight of the compound, from about 29% to about 30% methoxyl groups and from about 7% to about 12% hydroxylpropyl groups. HPMC 2910 is commercially available from the Dow Chemical Company under the tradename METHOCEL E. METHOCEL E5, which is one grade of HPMC-2910 suitable for use in the present invention, has a viscosity of about 4 to 6 cps (4 to 6 millipascal-seconds) at 20° C. in a 2% aqueous solution as determined by a Ubbelohde viscometer. Similarly, METHOCEL E6, which is another grade of HPMC-2910 suitable for use in the present invention, has a viscosity of about 5 to 7 cps (5 to 7 millipascal-seconds) at 20° C. in a 2% aqueous solution as determined by a Ubbelohde viscometer. METHOCEL E15, which is another grade of HPMC-2910 suitable for use in the present invention, has a viscosity of about 15000 cps (15 millipascal-seconds) at 20° C. in a 2% aqueous solution as determined by a Ubbelohde viscometer. As used herein, "degree of substitution" meand the average number of substituent groups attached to a anhydroglucose ring, and "hydroxypropyl molar substitution" meand the number of moles of hydroxypropyl per mole anhydroglucose.

One suitable polyvinyl alcohol and polyethylene glycol copolymer is commercially available from BASF Corporation under the tradename KOLLICOAT IR.

As used herein, "modified starches" include starches that have been modified by crosslinking, chemically modified for improved stability or optimized performance, or physically modified for improved solubility properties or optimized performance. Examples of chemically-modified starches are well known in the art and typically include those starches that have been chemically treated to cause replacement of some of its hydroxyl groups with either ester or ether groups. Crosslinking, as used herein, may occur in modified starches when two hydroxyl groups on neighboring starch molecules are chemically linked. As used herein, "pre-gelatinized starches" or "instantized starches" refers to modified starches that have been pre-wetted, then dried to enhance their cold-water solubility. Suitable modified starches are commercially available from several suppliers such as, for example, A. E. Staley Manufacturing Company, and National Starch & Chemical Company. One suitable film forming modified starch includes the pre-gelatinized waxy maize derivative starches that are commercially available from National Starch & Chemical Company under the tradenames PURITY GUM and FILMSET, and derivatives, copolymers, and mixtures thereof. Such waxy maize starches typically contain, based upon the total weight of the starch, from about 0 percent to about 18 percent of amylose and from about 100% to about 88% of amylopectin.

Other suitable film forming modified starches include the hydroxypropylated starches, in which some of the hydroxyl groups of the starch have been etherified with hydroxypropyl groups, usually via treatment with propylene oxide. One example of a suitable hydroxypropyl starch that possesses film-forming properties is available from Grain Processing Company under the tradename, PURE-COTE B790.

Suitable tapioca dextrins for use as film formers include those available from National Starch & Chemical Company under the tradenames CRYSTAL GUM or K-4484, and derivatives thereof such as modified food starch derived from tapioca, which is available from National Starch and Chemical under the tradename PURITY GUM 40, and copolymers and mixtures thereof.

Any thickener known in the art is suitable for use in the flowable material of the present invention. Examples of such thickeners include but are not limited to hydrocolloids (also referred to herein as gelling polymers), clays, gelling starches, and crystallizable carbohydrates, and derivatives, copolymers and mixtures thereof.

Examples of suitable hydrocolloids (also referred to herein as gelling polymers) such as alginates, agar, guar gum, locust bean, carrageenan, tara, gum arabic, tragacanth, pectin, xanthan, gellan, maltodextrin, galactomannan, pusstulan, laminarin, scleroglucan, gum arabic, inulin, pectin, whelan, rhamsan, zooglan, methylan, chitin, cyclodextrin, chitosan. Examples of suitable clays include smectites such as bentonite, kaolin, and laponite; magnesium trisilicate, magnesium aluminum silicate, and the like, and derivatives and mixtures thereof. Examples of suitable gelling starches include acid hydrolyzed starches, and derivatives and mixtures thereof. Additional suitable thickening hydrocolloids include low-moisture polymer solutions such as mixtures of gelatin and other hydrocolloids at water contents up to about 30%, such as for example those used to make "gummi" confection forms.

Additional suitable thickeners include crystallizable carbohydrates, and the like, and derivatives and combinations thereof. Suitable crystallizable carbohydrates include the monosaccharides and the oligosaccharides. Of the monosaccharides, the aldohexoses e.g., the D and L isomers of allose, altrose, glucose, mannose, gulose, idose, galactose, talose, and the ketohexoses e.g., the D and L isomers of fructose and sorbose along with their hydrogenated analogs: e.g., glucitol (sorbitol), and mannitol are preferred. Of the oligosaccharides, the 1,2-disaccharides sucrose and trehalose, the 1,4-disaccharides maltose, lactose, and cellobiose, and the 1,6-disaccharides gentiobiose and melibiose, as well as the trisaccharide raffinose are preferred along with the isomerized form of sucrose known as isomaltulose and its hydrogenated analog isomalt. Other hydrogenated forms of reducing disaccharides (such as maltose and lactose), for example, maltitol and lactitol are also preferred. Additionally, the hydrogenated forms of the aldopentoses: e.g., D and L ribose, arabinose, xylose, and lyxose and the hydrogenated forms of the aldotetroses: e.g., D and L erythrose and threose are preferred and are exemplified by xylitol and erythritol, respectively.

In one embodiment of the invention, the flowable material comprises gelatin as a gelling polymer. Gelatin is a natural, thermogelling polymer. It is a tasteless and colorless mixture of derived proteins of the albuminous class which is ordinarily soluble in warm water. Two types of gelatin—Type A and Type B—are commonly used. Type A gelatin is a derivative of acid-treated raw materials. Type B gelatin is a derivative of alkali-treated raw materials. The moisture content of gelatin, as well as its Bloom strength, composition and original gelatin processing conditions, determine its transition temperature between liquid and solid. Bloom is a standard measure of the strength of a gelatin gel, and is roughly correlated with molecular weight. Bloom is defined as the weight in grams required to move a half-inch diameter plastic plunger 4 mm into a 6.67% gelatin gel that has been held at 10° C. for 17 hours. In a preferred embodiment, the flowable material is an aqueous solution comprising 20% 275 Bloom pork skin gelatin, 20% 250 Bloom Bone Gelatin, and approximately 60% water.

Suitable xanthan gums include those available from C. P. Kelco Company under the tradenames KELTROL 1000, XANTROL 180, or K9B310.

Suitable clays include smectites such as bentonite, kaolin, and laponite; magnesium trisilicate, magnesium aluminum silicate, and the like, and derivatives and mixtures thereof.

"Acid-hydrolyzed starch," as used herein, is one type of modified starch that results from treating a starch suspension with dilute acid at a temperature below the gelatinization point of the starch. During the acid hydrolysis, the granular form of the starch is maintained in the starch suspension, and the hydrolysis reaction is ended by neutralization, filtration and drying once the desired degree of hydrolysis is reached. As a result, the average molecular size of the starch polymers is reduced. Acid-hydrolyzed starches (also known as "thin boiling starches") tend to have a much lower hot viscosity than the same native starch as well as a strong tendency to gel when cooled.

"Gelling starches," as used herein, include those starches that, when combined with water and heated to a temperature sufficient to form a solution, thereafter form a gel upon cooling to a temperature below the gelation point of the starch. Examples of gelling starches include, but are not limited to, acid hydrolyzed starches such as that available from Grain Processing Corporation under the tradename PURE-SET B950; hydroxypropyl distarch phosphate such as that available from Grain Processing Corporation under the tradename, PURE-GEL B990, and mixtures thereof.

Suitable low-melting hydrophobic materials include fats, fatty acid esters, phospholipids, and waxes. Examples of suitable fats include hydrogenated vegetable oils such as for example cocoa butter, hydrogenated palm kernel oil, hydrogenated cottonseed oil, hydrogenated sunflower oil, and hydrogenated soybean oil; and free fatty acids and their salts. Examples of suitable fatty acid esters include sucrose fatty acid esters, mono, di, and triglycerides, glyceryl behenate, glyceryl palmitostearate, glyceryl monostearate, glyceryl tristearate, glyceryl trilaurylate, glyceryl myristate, Glyco-Wax-932, lauroyl macrogol-32 glycerides, and stearoyl macrogol-32 glycerides. Examples of suitable phospholipids include phosphotidyl choline, phosphotidyl serene, phosphotidyl enositol, and phosphotidic acid. Examples of suitable waxes include carnauba wax, spermaceti wax, beeswax, candelilla wax, shellac wax, microcrystalline wax, and paraffin wax; fat-containing mixtures such as chocolate; and the like.

Suitable non-crystallizable carbohydrates include non-crystallizable sugars such as polydextrose, and starch hydrolysates, e.g. glucose syrup, corn syrup, and high fructose corn syrup; and non-crystallizable sugar-alcohols such as maltitol syrup.

Suitable solvents for optional use as components of the flowable material for making the core or the shell by molding include water; polar organic solvents such as methanol, ethanol, isopropanol, acetone, and the like; and non-polar organic solvents such as methylene chloride, and the like; and mixtures thereof.

The flowable material for making cores or the shell by molding may optionally comprise adjuvants or excipients, which may comprise up to about 30% by weight of the flowable material. Examples of suitable adjuvants or excipients include plasticizers, detackifiers, humectants, surfactants, anti-foaming agents, colorants, flavorants, sweeteners, opacifiers, and the like. Suitable plasticizers for making the core, the shell, or a portion thereof, by molding include, but not be limited to polyethylene glycol; propylene glycol; glycerin; sorbitol; triethyl citrate; tribuyl citrate; dibutyl sebecate; vegetable oils such as castor oil, rape oil, olive oil, and sesame oil; surfactants such as polysorbates, sodium lauryl sulfates, and dioctyl-sodium sulfosuccinates; mono acetate of glycerol; diacetate of glycerol; triacetate of glycerol; natural gums; triacetin; acetyltributyl citrate; diethyloxalate; diethylmalate; diethyl fumarate; diethylmalonate; dioctylphthalate; dibutyl-succinate; glyceroltributyrate; hydrogenated castor oil; fatty acids; substituted triglycerides and glycerides; and the like and/or mixtures thereof. In one embodiment, the plasticizer is triethyl citrate. In certain embodiments, the shell is substantially free of plasticizers, i.e. contains less than about 1%, say less than about 0.01% of plasticizers.

In embodiments in which the shell is prepared using a solvent-free molding process, the shell typically comprises at least about 30 percent, e.g. at least about 45 percent by weight of a thermal-reversible carrier. The shell may optionally further comprise up to about 55 weight percent of a release-modifying excipient. The shell may optionally further comprise up to about 30 weight percent total of various plasticizers, adjuvants and excipients. In certain embodiments in which the shell is prepared by solvent-free molding, and functions to delay the release of one or more active ingredients from an underlying core, the release modifying excipient is preferably selected from swellable, erodible hydrophilic materials.

In embodiments in which the shell is prepared using a solvent-based molding process, the shell typically comprises at least about 10 weight percent, e.g. at least about 12 weight percent or at least about 15 weight percent or at least about 20 weight percent or at least about 25 weight percent of a film-former. Here, the shell may optionally further comprise up to about 55 weight percent of a release-modifying excipient. The shell may again also optionally further comprise up to about 30 weight percent total of various plasticizers, adjuvants, and excipients.

In embodiments in which the shell is applied to the cores by molding, at least a portion of the shell surrounds the cores such that the shell inner surface resides substantially conformally upon the outer surfaces of the cores. As used herein, the term "substantially conformally" means that the inner surface of the shell has peaks and valleys or indentations and protrusions corresponding substantially inversely to the peaks and valleys of the outer surface of the core. In certain such embodiments, the indentations and protrusions typically have a length, width, height or depth in one dimension of greater than 10 microns, say greater than 20 microns, and less than about 30,000 microns, preferably less than about 2000 microns.

The total weight of the shell is preferably about 20 percent to about 400 percent of the total weight of the cores. In embodiments wherein the shell is prepared by a solvent-free molding process, the total weight of the shell is typically from about 50 percent to about 400 percent, e.g. from about 75 percent to about 400 percent, or about 100 percent to about 200 percent of the total weight of the cores. In embodiments wherein the shell is prepared by a solvent-based molding process, the total weight of the shell is typically from about 20 percent to about 100 percent of the total weight of the cores.

The thickness of the shell is important to the release properties of the dosage form. Advantageously, the dosage forms of the invention can be made with precise control over shell thickness, in particular using the thermal cycle or thermal setting injection molding methods and apparatus described above. Typical shell thicknesses that may be employed are about 50 to about 4000 microns. In certain preferred embodiments, the shell has a thickness of less than 800 microns. In embodiments wherein the shell portion is prepared by a solvent-free molding process, the shell portion typically has a thickness of about 500 to about 4000 microns, e.g. about 500 to about 2000 microns, say about 500 to about 800 microns, or about 800 to about 1200 microns. In embodiments wherein the shell portion is prepared by a solvent-based molding process, the shell portion typically has a thickness of less than about 800 microns, e.g. about 100 to about 600 microns, say about 150 to about 400 microns. In a particularly preferred embodiment the dosage form comprises first and second cores and first and second shell portions, and at least one of the shell portions has a thickness of less than about 800 microns, e.g. about 100 to about 600 microns, e.g. about 150 to about 400 microns.

In embodiments in which the shell is prepared by molding, either by a solvent-free process or by a solvent-based process, the shell typically is substantially free of pores in the diameter range of 0.5 to 5.0 microns, i.e. has a pore volume in the pore diameter range of 0.5 to 5.0 microns of less than about 0.02 cc/g, preferably less than about 0.01 cc/g, more preferably less than about 0.005 cc/g. Typical compressed materials have pore volumes in this diameter range of more than about 0.02 cc/g. Pore volume, pore diameter and density may be determined using a Quantachrome Instruments PoreMaster 60 mercury intrusion porosimeter and associated computer software program known as "Porowin." The procedure is documented in the Quantachrome Instruments PoreMaster Operation Manual. The PoreMaster determines both pore volume and pore diameter of a solid or powder by forced intrusion of a non-wetting liquid (mercury), which involves evacuation of the sample in a sample cell (penetrometer), filling the cell with mercury to surround the sample with mercury, applying pressure to the sample cell by: (i) compressed air (up to 50 psi maximum); and (ii) a hydraulic (oil) pressure generator (up to 60000 psi maximum). Intruded volume is measured by a change in the capacitance as mercury moves from outside the sample into its pores under applied pressure. The corresponding pore size diameter (d) at which the intrusion takes place is calculated directly from the so-called "Washburn Equation": $d = -(4\gamma(\cos\theta)/P)$ where $\gamma$ is the surface tension of liquid mercury, $\theta$ is the contact angle between mercury and the sample surface and P is the applied pressure.

Equipment used for pore volume measurements:
1. Quantachrome Instruments PoreMaster 60.
2. Analytical Balance capable of weighing to 0.0001 g.
3. Desiccator.

Reagents used for measurements:
1. High purity nitrogen.
2. Triply distilled mercury.
3. High pressure fluid (Dila AX, available from Shell Chemical Co.).
4. Liquid nitrogen (for Hg vapor cold trap).
5. Isopropanol or methanol for cleaning sample cells.
6. Liquid detergent for cell cleaning.

Procedure:
The samples remain in sealed packages or as received in the dessicator until analysis. The vacuum pump is switched on, the mercury vapor cold trap is filled with liquid nitrogen, the compressed gas supply is regulated at 55 psi., and the instrument is turned on and allowed a warm up time of at least 30 minutes. The empty penetrometer cell is assembled as described in the instrument manual and its weight is recorded. The cell is installed in the low pressure station and "evacuation and fill only" is selected from the analysis menu, and the following settings are employed:
  Fine Evacuation time: 1 min.
  Fine Evacuation rate: 10
  Coarse Evacuation time: 5 min.

The cell (filled with mercury) is then removed and weighed. The cell is then emptied into the mercury reservoir, and two tablets from each sample are placed in the cell and the cell is reassembled. The weight of the cell and sample are then recorded. The cell is then installed in the low-pressure station, the low-pressure option is selected from the menu, and the following parameters are set:
  Mode: Low pressure
  Fine evacuation rate: 10
  Fine evacuation until: 200 µHg
  Coarse evacuation time: 10 min.
  Fill pressure: Contact +0.1
  Maximum pressure: 50
  Direction: Intrusion And Extrusion
  Repeat: 0
  Mercury contact angle: 140
  Mercury surface tension: 480

Data acquisition is then begun. The pressure vs. cumulative volume-intruded plot is displayed on the screen. After low-pressure analysis is complete, the cell is removed from the low-pressure station and reweighed. The space above the mercury is filled with hydraulic oil, and the cell is assembled and installed in the high-pressure cavity. The following settings are used:
  Mode: Fixed rate
  Motor speed: 5
  Start pressure: 20
  End pressure: 60,000
  Direction: Intrusion and extrusion
  Repeat: 0
  Oil fill length: 5
  Mercury contact angle: 140
  Mercury surface tension: 480

Data acquisition is then begun and graphic plot pressure vs. intruded volume is displayed on the screen. After the high pressure run is complete, the low- and high-pressure data files of the same sample are merged.

In those embodiments in which solvent-free molding is employed, the flowable material may comprise a thermal-reversible carrier. Suitable thermal-reversible carriers for use in making a core, the shell or both by molding are thermoplastic materials typically having a melting point below about 110° C., more preferably between about 20 and about 100° C. Examples of suitable thermal-reversible carriers for solvent-free molding include thermplastic polyalkalene glycols, thermoplastic polyalkalene oxides, low melting hydrophobic materials, thermoplastic polymers, thermoplastic starches, and the like. Preferred thermal-reversible carriers include polyethylene glycol and polyethylene oxide. Suitable thermoplastic polyalkylene glycols for use as thermal-reversible carriers include polyethylene glycol having molecular weight from about 100 to about 20,000, e.g. from about 100 to about 8,000 Daltons. Suitable thermoplastic polyalkalene oxides include polyethylene oxide having a molecular weight from about 100,000 to about 900,000 Daltons. Suitable low-melting hydrophobic materials for use as thermal-reversible carriers include fats, fatty acid esters, phospholipids, and waxes which are solid at room temperature, fat-containing mixtures such as chocolate; and the like. Examples of suitable fats include hydrogenated vegetable oils such as for example cocoa butter, hydrogenated palm kernel oil, hydrogenated cottonseed oil, hydrogenated sunflower oil, and hydrogenated soybean oil; and free fatty acids and their salts. Examples of suitable fatty acid esters include sucrose fatty acid esters, mono, di, and triglycerides, glyceryl behenate, glyceryl palmitostearate, glyceryl monostearate, glyceryl tristearate, glyceryl trilaurylate, glyceryl myristate, Glyco-Wax-932, lauroyl macrogol-32 glycerides, and stearoyl macrogol-32 glycerides. Examples of suitable phospholipids include phosphotidyl choline, phosphotidyl serene, phosphotidyl enositol, and phosphotidic acid. Examples of suitable waxes which are solid at room temperature include carnauba wax, spermaceti wax, beeswax, candelilla wax, shellac wax, microcrystalline wax, and paraffin wax. Suitable thermoplastic polymers for use as thermal-reversible carriers include thermoplastic water swellable cellulose derivatives, thermoplastic water insoluble polymers, thermoplastic vinyl polymers, thermoplastic starches, and thermoplastic resins, and combinations thereof. Suitable thermoplastic water swellable cellulose derivatives include include hydroxypropylmethyl cellulose (HPMC), methyl cellulose (MC), carboxymethylcellulose (CMC), cross-linked hydroxypropylcellulose, hydroxypropyl cellulose (HPC), hydroxybutylcellulose (HBC), hydroxyethylcellulose (HEC), hydroxypropylethylcellulose, hydroxypropylbutylcellulose, hydroxypropyleth-ylcellulose, and salts, derivatives, copolymers, and combinations thereof. Suitable thermoplastic water insoluble polymers include ethylcellulose, polyvinyl alcohols, polyvinyl acetate, polycaprolactones, cellulose acetate and its derivatives, acrylates, methacrylates, acrylic acid copolymers, and the like and derivatives, copolymers, and combinations thereof. Suitable thermoplastic vinyl polymers include polyvinylacetate, polyvinyl alcohol, and polyvinyl pyrrolidone (PVP). Examples of suitable thermoplastic starches for use as thermal-reversible carriers are disclosed for example in U.S. Pat. No. 5,427,614. Examples of suitable thermoplastic resins for use as themal-reversible carriers include dammars, mastic, rosin, shellac, sandarac, and glcerol ester of rosin. In one embodiment, the thermal-reversible carrier for making a core by molding is selected from polyalkylene glycols, polyalkaline oxides, and combinations thereof.

In embodiments in which the shell comprises an active ingredient intended to have immediate release from the dosage form, the shell is preferably prepared via solvent-free molding. In such embodiments a thermal-reversible carrier is employed in the flowable material to make the shell, said thermal-reversible carrier preferably selected from polyethylene glycol with weight average molecular weight from about 1450 to about 20000, polyethylene oxide with weight average molecular weight from about 100,000 to about 900,000, and the like.

In certain embodiments of the invention, the shell, or a shell portion may function as a diffusional membrane which contains pores through which fluids can enter the dosage form, contact and dissolve active ingredient in the core, which can then be released in a sustained, extended, prolonged or retarded manner. In these embodiments, the rate of release of active ingredient from an underlying core portion will depend upon the total pore area in the shell portion, the pathlength of the pores, and the solubility and diffusivity of the active ingredient (in addition to its rate of release from the core portion itself). In preferred embodiments in which a shell portion functions as a diffusional membrane, the release of the active ingredient from the dosage form may be described as controlled, prolonged, sustained or extended. In these embodiments, the contribution to active ingredient dissolution from the shell may follow zero-order, first-order, or square-root of time kinetics. In certain such embodiments, the shell portion preferably comprises a release modifying moldable excipient comprising a combination of a pore former and an insoluble edible material, for example a film forming water insoluble polymer. Alternately, in embodiments in which the shell portion is prepared by solvent-free molding, described below, the shell portion may comprise a thermal-reversible carrier that functions by dissolving and forming pores or channels through which the active ingredient may be liberated.

In certain other embodiments, the shell or a shell portion functions as an eroding matrix from which active ingredient dispersed in the shell is liberated by the dissolution of successive layers of the shell surface. In these embodiments, the rate of active ingredient release will depend on the dissolution rate of the matrix material in the shell or shell portion. Particularly useful matrix materials for providing surface erosion include those that first absorb liquid, then swell and/or gel prior to dissolving. In certain such embodiments, the shell or shell portion preferably comprises a release modifying moldable excipient comprising a swellable erodible hydrophilic material.

In certain other embodiments, the shell or a portion thereof functions as a barrier to prevent release therethrough of an active ingredient contained in an underlying core. In such embodiments, active ingredient is typically released from a portion of the core that is not covered by that portion of the shell, for example from a portion of the core in communication with one or more openings in the shell. Such embodiments advantageously allow for control of the surface area for release of the active ingredient. In certain embodiments for example, the surface area for release of active ingredient can be maintained substantially constant over time. In a particularly preferred embodiment, the release of at least one active ingredient follows substantially zero-order kinetics. In such embodiments, the shell preferably comprises a modified release composition comprising a water insoluble material, for example a water insoluble polymer.

In other embodiments, the shell, or a shell portion functions as a delayed release coating to delay release of one or more active ingredients contained in an underlying core. In these embodiments, the lag-time for onset of active ingredient release may be governed by erosion of the shell, diffusion of active ingredient through the shell, or a combination thereof.

In certain such embodiments, the shell preferably comprises a release modifying moldable excipient comprising a swellable erodible hydrophilic material.

The following non-limiting example further illustrates the claimed invention.

EXAMPLE

A dosage form according to the invention providing a double pulse release of ibuprofen is manufactured by a solvent-free molding process as follows. The double pulse consists of a 200 mg immediate release (IR) ibuprofen followed by a 100 mg burst release of ibuprofen after a predetermined lag time.

Part A. Preparation of the 100 mg Immediate-Release (IR) Ibuprofen Core Formulation:

| Ingredient | Trade Name | Manufacturer | Mg/Tablet |
|---|---|---|---|
| Ibuprofen (115 microns) | | Albemarle Corp. Orangeburg, SC | 100.0 |
| Microcrystalline cellulose | Avicel pH 101 ® | FMC Corp. Newark, DE 19711 | 106.5 |
| Sodium starch glycolate | Explotab ® | Penwest Pharmaceuticals Co. Patterson, NJ | 6.0 |
| Colloidal silicon dioxide | Cab-O-Sil LM-5 ® | Cabot Corp. Tuscola, IL | 0.5 |
| Total | | | 213.0 |

Manufacturing Process:

Ibuprofen, microcrystalline cellulose and sodium starch glycolate are delumped through a 30 mesh screen and said ingredients are mixed in a 2 qt. P-K blender for 5 minutes. Colloidal silicon dioxide is also delumped through a 30 mesh screen and is added to the aforementioned mixture for blending for another 5 minutes.

A Beta tablet press (Manesty, Liverpool, UK) equipped with round punch and die unit with a diameter of 0.250" is used to make the first core as a tablet. The final blend (from Step 1) is fed into the die and is compressed into a tablet core under 2000 lb/in$^2$ of operating pressure. The weight of compressed tablet is 213.0 mg, which contains 100.0 mg of ibuprofen.

Part B. Preparation of the 200 mg Immediate-Release (IR) Ibuprofen Core Formulation:

| Ingredients | Trade Name | Manufacturer | Mg/Tablet |
|---|---|---|---|
| Ibuprofen granules (115 microns) | | Albemarle Corp. Orangeburg, SC | 200.0 |
| Sodium starch glycolate | Explotab ® | Penwest Pharmaceuticals Co. Patterson, NJ | 12.0 |
| Colloidal silicon dioxide | Cab-O-Sil LM-5 ® | Cabot Corp. Tuscola, IL | 1.0 |
| Total | | | 213.0 |

Manufacturing Process:

Ibuprofen and sodium starch glycolate are delumped through a 30 mesh screen and said ingredients are mixed in a 2 qt. P-K blender for 5 minutes. Colloidal silicon dioxide is also delumped through a 30 mesh screen and is added to the aforementioned mixture for blending for another 5 minutes. Prescreened (through a 30 mesh screen) ibuprofen and sodium starch glycolate are mixed in a 2 qt. P-K blender for 5 minutes.

The final blend (from Step 1) is fed into the die of the tablet press described in Part A and is compressed into a tablet core under 2000 lb/in$^2$ of operating pressure. The weight of compressed tablet is 213.0 mg, which contains 200.0 mg of ibuprofen.

Part C. Application of the Shell by Solvent-Free Molding

Shell Formulation:

| Ingredient | Trade Name | Manufacturer | Mg/Tablet |
|---|---|---|---|
| Polyethylene Glycol 8000 | Carbowax ® | Union Carbide Corporation, Danbury, CT 06817-0001 | 149.1 |
| Polyethylene Oxide (MW 200,000) | Polyox ® WSR N-80 | Union Carbide Corporation, Danbury, CT 06817-0001 | 42.6 |
| Hydroxypropyl Methylcellulose | Methocel K15M Perm CR | The Dow Chemical Co., Midland, Michigan, 48674 | 63.9 |
| Triethyl Citrate | | Morflex, Inc., Greensboro, North Carolina 27403 | 85.2 |
| Lauroyl Macrogol-32 Glycerides | Gelucire 50/13 | Gattefosse Corp., Westwood, NJ 07675 | 85.2 |

Manufacturing Process:

A beaker is submersed in a water bath (Ret digi-visc; Antal-Direct, Wayne, Pa. 19087) where the water bath temperature is set at 85° C. Polyethylene glycol (PEG) 8000 and Gelucire 50/13 are added to the beaker and are mixed with a spatula until all PEG and Gelucire are melted. Hydroxypropyl methylcellulose is added to the molten mixture and is mixed for 10 minutes. Triethyl Citrate is added to the molten mixture and is mixed for 2 minutes. Polyethylene Oxide 200,000 is added and is mixed for 20 minutes. The shell material is provided in flowable form.

A laboratory scale thermal cycle molding unit having an overall caplet shape of dimensions of 0.700"×0.350"×0.06", is used to apply first and second shell portions to the cores. The molding unit comprises a single mold assembly made from an upper mold assembly portion comprising an upper mold cavity, and a lower mold assembly portion comprising a lower mold cavity. The lower mold assembly portion is first cycled to a hot stage at 85° C. for 30 seconds. The shell material of Part C is introduced into the lower mold cavity. Two separate cores prepared as described in aforementioned Parts A and B are then inserted into two stations within the cavity. The stations separate the two cores within the lower mold cavity by 1 mm. A blank upper mold assembly portion is mated with the lower mold assembly portion. The mold assembly is then cycled to a cold stage at 5° C. for 60 seconds to harden the first shell portion. The blank mold assembly portion is removed from the lower mold assembly portion. The upper mold assembly portion is cycled to a hot stage at 85° C. for 30 seconds. The shell material is added to the upper mold cavity.

The upper mold cavity comprises a small rod (0.1 mm in diameter×1 mm in length) attached to its inner surface that contacts one station for one of the cores. The lower mold assembly portion, which has been maintained at 5° C., is mated with the upper mold assembly portion in such a way that the first core of Part B (200 mg of ibuprofen tablet) is mated with the first core station of the upper mold assembly.

The upper mold assembly portion is then cycled to a cold stage at 5° C. for 120 seconds to harden the second shell portion. The lower mold assembly portion is then removed and the finished dosage form, a molded caplet coated with two halves of the same shell material, is ejected from the upper mold cavity. The weight gain from the shell material (i.e. the difference in weight between the finished dosage form and the core) is recorded.

We claim:

1. A dosage form comprising at least one active ingredient, a first core, and a second core, said first and second cores each being surrounded by a shell, wherein the shell comprises a plurality of openings and provides for modified release of at least one active ingredient upon contact of the dosage form with a liquid medium, at least one of the first or second cores being distal to all of the openings and wherein the shell has a pore volume in the pore diameter range of 0.5 to 5.0 microns of less than 0.02 cc/g.

2. The dosage form of claim 1, wherein all the openings are proximal to only the first core.

3. The dosage form of claim 1, wherein the openings contact the first core.

4. The dosage form of claim 1, wherein all the openings contact only the first core.

5. The dosage form of claim 1, wherein the shell comprises a release modifying moldable excipient.

6. The dosage form of claim 5, wherein the release modifying moldable excipient is selected from the group consisting of swellable erodible hydrophilic materials, pH-dependent polymers, pore formers, insoluble edible materials and combinations thereof.

7. The dosage form of claim 1, wherein the shell comprises a thermal-reversible carrier selected from the group consisting of polyethylene glycol, polyethylene oxide and combinations thereof.

8. The dosage form of claim 5, wherein the release modifying excipient is selected from the group consisting of shellac, hydroxypropylmethylcellulose, polyethylene oxide, ammonio methacrylate copolymer type B, and combinations thereof.

9. The dosage form of claim 1, wherein the shell comprises a film-former selected from the group consisting of cellulose acetate, ammonio methacrylate copolymer type B, shellac, hydroxypropylmethylcellulose, and combinations thereof.

10. The dosage form of claim 6, wherein the swellable erodible hydrophilic material is selected from the group consisting of cross-linked polyvinyl pyrrolidone, cross-linked agar, cross-linked carboxymethylcellulose sodium, and combinations thereof.

11. The dosage form of claim 1, wherein the shell comprises a plasticizer.

12. The dosage form of claim 1, wherein the shell comprises a pore former.

13. The dosage form of claim 1, wherein at least one core comprises active ingredient.

14. The dosage form of claim 1, wherein at least one core comprises two or more layers.

15. The dosage form of claim 1, wherein at least one of the first or second cores comprises a compressed tablet.

16. The dosage form of claim 1, wherein at least one of the first or second cores comprises a multi-layer tablet.

17. The dosage form of claim 1, wherein at least one of the first or second cores comprises particles comprising one or more active ingredients.

18. The dosage form of claim 17, wherein at least a portion of the particles comprise a coating capable of providing modified release of the active ingredient upon contacting of the particles with a liquid medium.

19. The dosage form of claim 1, wherein the first and second cores have the same composition.

20. The dosage form of claim 1, wherein the first and second cores have the same physical dimensions.

21. The dosage form of claim 1, wherein the first and second cores comprise different active ingredients.

22. The dosage form of claim 1, wherein the first and second cores have different compositions.

23. The dosage form of claim 1, wherein the first and second cores have different physical dimensions.

24. The dosage form of claim 1, wherein the shell comprises active ingredient.

25. The dosage form of claim 1, wherein the first core comprises active ingredient that is released immediately from the dosage form upon contacting of the dosage form with a liquid medium.

26. The dosage form of claim 1, wherein the shell provides for delayed, sustained, prolonged, extended, or retarded release of at least one active ingredient contained in the second core.

27. The dosage form of claim 1, wherein the openings provide for immediate release of at least one active ingredient contained in the first core, and wherein the shell provides for delayed release of at least one active ingredient contained in the second core, upon contacting of the dosage form with a liquid medium.

28. The dosage form of claim 1, wherein the dosage form provides delayed release of at least one active ingredient upon contacting of the dosage form with a liquid medium.

29. The dosage form of claim 1, wherein the dosage form provides immediate release of at least one active ingredient upon contacting of the dosage form with a liquid medium.

30. The dosage form of claim 1, wherein the dosage form provides immediate release of at least one active ingredient from a first core upon contacting of the dosage form with a liquid medium, followed by a time delay, followed by release of at least one active ingredient from a second core.

31. The dosage form of claim 1, wherein the first and second cores each comprise active ingredients and the active ingredients have release profiles that are substantially different from one another.

32. The dosage form of claim 30, wherein the active ingredient in the first core has an immediate release profile and the active ingredient in the second core has a modified release profile.

33. The dosage form of claim 1, further comprising an outer coating covering at least a portion of the shell.

34. The dosage form of claim 1, wherein the shell comprises a first shell portion and a second shell portion.

35. The dosage form of claim 34, wherein the first and second shell portions are compositionally different.

36. The dosage form of claim 34, wherein each core comprises upper and lower faces and the first shell portion is in contact with the upper face of each core, and the second shell portion is in contact with the lower face of each core.

37. The dosage form of claim 34, wherein the first shell portion is in contact with the first core, and the second shell portion is in contact with the second core.

38. The dosage form of claim 34, wherein the first shell portion comprises one or more openings, and the second shell portion is substantially free of openings.

39. The dosage form of claim 1, wherein the first and second cores are separated by an interior wall of the shell.

40. The dosage form of claim 39, wherein the thickness of the interior wall is about 10% to about 200% of the thickness of at least one of the first or second cores.

41. The dosage form of claim 1, wherein the openings extend only partially through the shell.

42. A dosage form comprising a first core containing a pharmaceutically effective dose of a first active ingredient, and a second core containing a pharmaceutically effective dose of a second active ingredient, said first and second cores each being surrounded by a shell, wherein the shell comprises a plurality of openings, provides for modified release of the second active ingredient upon contact of the dosage form with a liquid medium and has a pore volume in the pore diameter range of 0.5 to 5.0 microns of less than 0.02 cc/g, wherein the second core is located distal to all the openings, and all the openings are proximal to only the first core.

43. The dosage form of claim 42, wherein the first active ingredient is selected from the group consisting of acetaminophen, acetyl salicylic acid, ibuprofen, naproxen, ketoprofen, flurbiprofen, diclofenac, cyclobenzaprine, meloxicam, rofecoxib, celecoxib, and pharmaceutically acceptable salts, esters, isomers, and mixtures thereof.

44. The dosage form of claim 43, wherein the first and second active ingredients are both selected from the group consisting of ibuprofen, and pharmaceutically acceptable salts, esters, isomers, and mixtures thereof.

45. The dosage form of claim 43, wherein the first active ingredient is selected from the group consisting of ibuprofen, and pharmaceutically acceptable salts, esters, isomers, and mixtures thereof, and the second active ingredient is selected from the group consisting of acetaminophen, and pharmaceutically acceptable salts, esters, isomers, and mixtures thereof.

* * * * *

UNITED STATES PATENT AND TRADEMARK OFFICE
CERTIFICATE OF CORRECTION

PATENT NO. : 7,416,738 B2
APPLICATION NO. : 10/393871
DATED : August 26, 2008
INVENTOR(S) : Harry S. Sowden et al.

It is certified that error appears in the above-identified patent and that said Letters Patent is hereby corrected as shown below:

Col. 31, line 36, Claim 8 should read: "The dosage form of claim 6, wherein the release modifying excipient is selected from the group consisting of shellac, hydroxypropylmethylcellulose, polyethylene oxide, ammonio methacrylate copolymer type B, and combinations thereof."

Signed and Sealed this

Twentieth Day of October, 2009

David J. Kappos
*Director of the United States Patent and Trademark Office*